(12) United States Patent
Schnidler et al.

(10) Patent No.: US 6,844,347 B1
(45) Date of Patent: Jan. 18, 2005

(54) SUBSTITUTED 4-AMINO-2ARYL-PYRIMIDINES, THEIR PRODUCTION AND USE AND PHARMACEUTICAL PREPARATIONS CONTAINING SAME

(75) Inventors: Ursula Schnidler, Bad Soden (DE); Karl Schoenafinger, Alzenau (DE); Hartmut Strobel, Liederbach (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/762,893

(22) PCT Filed: Aug. 4, 1999

(86) PCT No.: PCT/EP99/05636

§ 371 (c)(1),
(2), (4) Date: Feb. 13, 2001

(87) PCT Pub. No.: WO00/09496

PCT Pub. Date: Feb. 24, 2000

(30) Foreign Application Priority Data

Aug. 13, 1998 (DE) .......................... 198 36 697

(51) Int. Cl.$^7$ ........................ A61K 31/50; C07D 239/42
(52) U.S. Cl. ............ 514/256; 514/211.09; 514/217.06; 514/218; 514/232.2; 514/235.8; 540/544; 540/545; 540/601; 544/58.6; 544/60; 544/82; 544/122; 544/295; 544/326; 544/327; 544/329
(58) Field of Search .................... 544/326, 327, 544/329, 295, 82, 122, 58.6, 60; 540/601, 544, 545; 514/211, 232.12, 217.6, 212, 218, 256, 235.8, 235.3

(56) References Cited

U.S. PATENT DOCUMENTS

| 4,493,726 A | 1/1985 | Burdeska et al. ............ 544/334 |
| 6,162,819 A | 12/2000 | Schindler et al. ............ 514/183 |

FOREIGN PATENT DOCUMENTS

| DE | 4034762 A1 | 5/1992 |
| DE | 19744027 A1 | 4/1999 |
| DE | 19756388 A1 | 6/1999 |
| EP | 0 055 693 | 12/1980 |
| EP | 0 136 976 A2 | 4/1985 |
| EP | 0 555 478 A1 | 8/1993 |
| EP | 0 908 456 A1 | 4/1999 |
| JP | 06-192252 | 7/1994 |
| WO | WO 98/37079 | 8/1998 |

OTHER PUBLICATIONS

Morel et al., Chemical Abstracts, vol. 125:221520, 1995.*
Brown et al., Chemical Abstracts, vol. 100:209733, 1984.*
Abstract for German Patent No. DE 19744027 A1, Schindler et al., "New Pyrazolo(3,4–b)pyridine Derivatives Useful as cGMP Agonists", Derwent WPI database, no date.
Abstract for German Patent No. DE 4034762 A, Braun et al., "Pyridyl Pyrimidine Derivs. are Fungicides for Plant Protection and for Protecting and preserving Industrial Materials", Derwent WPI database, no date.
Abstract for German Patent No. DE 19756388 A, Schindler et al., "New 2–aryl–4–amino–6,7–dimethoxy–quinazoline Derivatives Useful as Guanylate Cycloase Activators for Treating Cardiovascular Diseases, etc.", Derwent WPI database, no date.
Ignarro, Louis J., "Regulation of Cytosolic Guanylyl Cyclase by Porphyrins and Metalloporphyrins," *Advances in Pharmacology* 26:35–65 (1994).
Abstract for Japanes Patent No. 06192252, Ito Yoichi, "Pyrazine Derivative and Herbicide", Patent Abstracts of Japan. no date.
Abstract for EP Patent No. EP0136976, Seiler Alfred et al, "Use of Phenyl Pyrimidines as Plant Regulators", esp@cenet database, no date.
Nikolaenkova E.B. et al., "Synthesis of 4,6–Bis(1H,2, 3–Triazolyl)Pyrimidines by the Reaction of 4,6–Diazido–2–(4–Methoxyphenyl)–Pyrimidine with Compounds Containing a Reactive Methylene Group," *Chemistry of Heterocyclic Compounds* 33(8):968–972 (1998).
Mülsch, Alexander et al., "Purification of Heme–Containing Soluble Guanylyl Cyclase," *Methods in Enzymology* 195:377–383 (1991).
Ko, Feng–Nien et al., "YC–1, a Novel Activator of Platelet Guanylate Cyclase," *Blood* 84(12):4226–1233 (1994).
Vesely, David L., "Phencyclidine Stimulates Guanylate Cyclase Activity," *Biochemical and Biophysical Research Communications* 88(4):1244–1248 (1979).

(List continued on next page.)

Primary Examiner—Richard L. Raymond
(74) Attorney, Agent, or Firm—Finnegan, Henderson, Farabow, Garrett & Dunner, L.L.P.

(57) ABSTRACT

The invention relates to compounds of formula I,

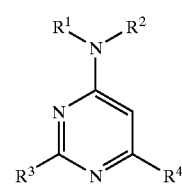

in which $R^1$, $R^2$, $R^3$ and $R^4$ have the meanings given in the claims. Said compounds are valuable active ingredients for the treatment and prophylaxis of diseases, for example of cardiovascular diseases such as hypertension, angina pectoris, heart failure, thrombosis or atherosclerosis. The compounds of the formula I are able to modulate the body's production of cyclic guanosine monophosphate (cGMP) and are generally suitable for the treatment and prophylaxis of disorders associated with impaired cGMP balance. The invention furthermore relates to methods for producing compounds of the formula I, their use in the treatment and prophylaxis of the above diseases and in the preparation of medicaments for such diseases, and pharmaceutical preparations containing the compounds of formula I.

27 Claims, No Drawings

OTHER PUBLICATIONS

Vesely, D.L., et al., "B Complex Vitiamins Activate Rat Guanylate Cyclase and Increase Cyclic GMP Levels," *European Journal of Clinical Investigation* 15:258–262 (1985).

Pettibone, D.J., et al., "A Structurally Novel Stimulator of Guanylate Cyclase with Long–Lasting Hypotensive Activity in the Dog," *European Journal of Pharmacology* 116:307–312 (1985).

Yu, S–M., et al., "Vasorelaxant Effect of Isoliquiritigenin, a Novel Soluble Guanylate Cyclaes Activator, in Rat Aorta," *British Journal of Phramacology* 114:1587–1594 (1995).

Yu, S–M., et al., "Mechanism of Anti–Proliferation Caused by YC–1, an Indazole Derivative, in Cultured Rat A10 Vascular Smooth–Muscle Cells," *Biochem. J.* 306:787–792 (1995).

Wu, Chin–Chung et al., "YC–1 Inhibited Human Platelet Aggregation Through NO–Independent Activation of Soluble Guanylate Cyclase," *British Journal of Pharmacology* 116:1973–1978 (1995).

Ignarro, Louis J., "Regulation of Cytosolic Guanylyl Cyclase by Porphyrins and Metalloporphyrins," *Advances in Pharmacology* 26:35–65 (1994).

Abstract for Japanese Patent No. 06192252, Ito Yoichi, "Pyrazine Derivative and Herbicide", Patent Abstracts of Japan (Jul. 12, 1994).

Abstract for EP Patent No. EP0136976, Seiler Alfred et al., "Use of Phenyl Pyrimidines as Plant Regulators", esp@cenet database (Apr. 10, 1985).

Abstract for German Patent No. DE 19744027 A1, Schindler et al., "new Pyrazolo(3,4–b)pyridine Derivatives Useful as cGMP Agonists", Derwent WPI database (Apr. 8, 1999).

Abstract for German Patent No. DE 4034762 A, Braun et al., "Pyridyl Pyrimidine Derivs.—are Fungicides for Plant Protection and for Protecting and Preserving Industrial Materials", Derwent WPI database (May 7, 1992).

Abstract for German Patent No. DE 19756388 A, Schindler et al., "New 2–aryl–4–amino–6,7–dimethoxy–quinazoline Derivatives Useful as Guanylate Cyclase Activators for Treating Cardiovascular Diseases, etc.", Derwent WPI database (Jun. 24, 1999).

Brown, Desmond J. et al., Heterocyclic Amplifiers of Phleomycin. I Some Pyrimidinylpurines, Pyrimidinylpteridines and Phenylpyrimidines,: Aust. J. Chem., 37:155–63 (1984).

Morel, Goerges et al., "2–Aza–1,3–Dienes with Electron–Relaesing Substituents at the 1,3 positions. Reagents for the Construction of Pyridine Derivatives." Tetrahedron, 52:10095–10112 (1996).

\* cited by examiner

SUBSTITUTED 4-AMINO-2ARYL-PYRIMIDINES, THEIR PRODUCTION AND USE AND PHARMACEUTICAL PREPARATIONS CONTAINING SAME

This application is a U.S. national stage filing of PCT International Application No. PCT/EP99/05636, filed on Aug. 4, 1999, which claims the benefit of priority to German Patent Application No. 198 36 697.3, filed on Aug. 13, 1998.

The present invention relates to compounds of the formula I,

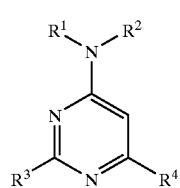

in which $R^1$, $R^2$, $R^3$ and $R^4$ have the meanings indicated below, which are valuable pharmaceutical active compounds for the therapy and prophylaxis of diseases, for example of cardiovascular disorders such as high blood pressure, angina pectoris, cardiac insufficiency, thromboses or atherosclerosis. The compounds of the formula I have the ability to modulate the endogenous production of cyclic guanosine monophosphate (cGMP) and are generally suitable for the therapy and prophylaxis of disease states which are associated with a disturbed cGMP balance. The invention furthermore relates to processes for the preparation of compounds of the formula I, their use for the therapy and prophylaxis of the designated disease states and for the production of pharmaceuticals therefor, and pharmaceutical preparations which contain compounds of the formula I.

cGMP is an important intracellular messenger, which elicits a number of pharmacological effects by means of the modulation of cGMP-dependent protein kinases, phosphodiesterases and ion channels. Examples are smooth muscle relaxation, the inhibition of platelet activation and the inhibition of smooth muscle cell proliferation and leukocyte adhesion. cGMP is produced by particulate and soluble guanylate cyclases as a response to a number of extracellular and intracellular stimuli. In the case of the particulate guanylate cyclases, the stimulation essentially takes place by means of peptide signal substances, such as the atrial natriuretic peptide or the cerebral natriuretic peptide. The soluble guanylate cyclases (sGC), which are cytosolic, heterodimeric heme proteins, however, are essentially regulated by a family of low molecular weight, enzymatically formed factors. The most important stimulant is nitrogen monoxide (NO) or a closely related species. The importance of other factors such as carbon monoxide or the hydroxyl radical is still largely unclarified. The binding of NO to the heme with formation of a pentacoordinated heme-nitrosyl complex is discussed as an activation mechanism of activation by NO. The release associated therewith of the histidine which is bound to the iron in the basal state converts the enzyme into the activated conformation.

Active soluble guanylate cyclases are each composed of one α- and one β-subunit. Several subtypes of the subunits are described, which differ from one another with respect to sequence, tissue-specific distribution and expression in various stages of development. The subtypes $\alpha_1$ and $\beta_1$ are mainly expressed in the brain and lung, while $\beta_2$ is especially found in liver and kidney. The subtype $\alpha_2$ was detected in human fetal brain. The subunits designated as $\alpha_3$ and $\beta_3$ were isolated from human brain and are homologous to $\alpha_1$ and $\beta_1$. More recent studies point to an $\alpha_{2i}$ subunit, which contains an insert in the catalytic domain. All subunits show great homology in the area of the catalytic domain. The enzymes probably contain one heme per heterodimer, which is bonded via $\beta_1$-Cys-78 and/or $\beta_1$-His-105 and is part of the regulatory center.

The formation of guanylate cyclase-activating factors can be decreased under pathological conditions or increased degradation thereof can take place as a result of the increased occurrence of free radicals. The decreased activation of the sGC resulting therefrom leads, via the attenuation of the respective cGMP-mediated cell response, for example, to an increase in the blood pressure, to platelet activation or to increased cell proliferation and cell adhesion. As a result, the formation of endothelial dysfunction, atherosclerosis, high blood pressure, stable and unstable angina pectoris, thromboses, myocardial infarct, strokes or erectile dysfunction occurs. The pharmacological stimulation of the sGC offers a possibility for the normalization of cGMP production and thus allows the treatment or prevention of illnesses of this type.

For the pharmacological stimulation of sGC, until now compounds were almost exclusively used whose action is based on an intermediate release of NO, for example organic nitrates. The disadvantage of this method of treatment lies in the development of tolerance and weakening of action and the higher dose which therefore becomes necessary.

Various sGC stimulators which do not act via a release of NO were described in a series of publications by Vesely. The compounds, which are mostly hormones, plant hormones, vitamins or, for example, natural substances such as lizard toxins, however, consistently show only weak effects on cGMP formation in cell lysates (D. L. Vesely, Eur. J. Clin. Invest. 15 (1985) 258; D. L. Vesely, Biochem. Biophys. Res. Comm. 88 (1979) 1244). Stimulation of heme-free guanylate cyclase by protoporphyrin IX was detected by Ignarro et al. (Adv. Pharmacol. 26 (1994) 35). Pettibone et al. (Eur. J. Pharmacol. 116 (1985) 307) describe a hypotensive action for diphenyliodonium hexafluorophoshate and attributed this to a stimulation of sGC. Isoliquiritiginin, which shows a relaxant action on isolated rat aortas, likewise activates sGC according to Yu et al. (Brit. J. Pharmacol. 114 (1995) 1587). Ko et al. (Blood 84 (1994) 4226), Yu et al. (Biochem. J. 306 (1995) 787) and Wu et al. (Brit. J. Pharmacol. 116 (1995) 1973) detected an sGC stimulating activity of 1-benzyl-3-(5-hydroxymethyl-2-furyl)indazole and demonstrated an antiproliferative and platelet-inhibiting action. Substituted pyrazoles and condensed pyrazoles which have an sGC-stimulating action are described in EP-A-908456 and DE-A-19744027, substituted quinazolines having an action of this type in DE-A-19756388.

Various 4-amino-2-arylpyrimidines are already known. For example, in EP-A-55693 pyrimidines are described which are substituted in the 2-position by a phenyl group and which are suitable as antidotes for the protection of crop plants against the phytotoxic action of herbicides. EP-A-136976 describes 2-phenylpyrimidines which are plant growth regulators. For certain 2-phenylpyrimidines which in the 4-position can carry, inter alia, an amino group as a substituent, EP-A-555478 describes that they improve learning power and memory power.

Surprisingly, it has now been found that the pyrimidines of the formula I according to the invention bring about strong guanylate cyclase activation, on account of which they are suitable for the therapy and prophylaxis of illnesses which are associated with a low cGMP level.

The present invention thus relates to compounds of the formula I

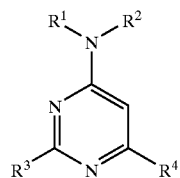

in which

R¹ is $(C_1-C_8)$-alkyl which can be substituted by one or more identical or different substituents from the group consisting of hydroxyl, $(C_1-C_4)$-alkoxy, $(C_1-C_4)$-alkyl-$S(O)_m$—, $R^5R^6N$ and aryl, $(C_3-C_9)$-cycloalkyl which can be substituted by one or more identical or different substituents from the group consisting of $(C_1-C_4)$-alkyl, hydroxyl and amino, or the radical of a 5-membered to 7-membered saturated heterocyclic ring which contains one or two identical or different hetero ring members from the group consisting of O, $NR^7$ and $S(O)_m$ and which can be substituted by one or more identical or different substituents from the group consisting of $(C_1-C_4)$-alkyl and aryl-$(C_1-C_4)$-alkyl-; and R² is hydrogen, $(C_1-C_8)$-alkyl which can be substituted by one or more identical or different substituents from the group consisting of hydroxyl, $(C_1-C_4)$-alkoxy, $(C_1-C_4)$-alkyl —$S(O)_m$—, $R^5 R^6N$ and aryl, $(C_3-C_9)$-cycloalkyl which can be substituted by one or more identical or different substituents from the group consisting of $(C_1-C_4)$-alkyl, hydroxyl and amino, or the radical of a 5-membered to 7-membered saturated heterocyclic ring which contains one or two identical or different hetero ring members from the group consisting of O, $NR^7$ and $S(O)_m$ and which can be substituted by one or more identical or different substituents from the group consisting of $(C_1-C_4)$-alkyl and aryl-$(C_1-C_4)$-alkyl-; or $R^1R^2N$ is a radical, bonded via a ring nitrogen atom, of a 5-membered to 7-membered saturated heterocyclic ring which, in addition to the nitrogen atom carrying the radicals R¹ and R², can contain a further hetero ring member from the group consisting of O, $NR^7$ and $S(O)_m$ and which can be substituted by one or more identical or different substituents from the group consisting of $(C_1-C_4)$-alkyl, hydroxyl, $(C_1-C_4)$-alkoxy, $R^8R^9N$, hydroxycarbonyl, $(C_1-C_4)$-alkoxycarbonyl and $R^8R^9N$—CO—;

R³ is aryl;

R⁴ is $(C_2-C_5)$-alkyl, trifluoromethyl or aryl;

R⁵ and R⁶ are identical or different radicals from the group consisting of hydrogen and $(C_1-C_4)$-alkyl or the group $R^5R^6N$ is a radical, bonded via a ring nitrogen atom, of a 5-membered to 7-membered saturated or unsaturated heterocyclic ring which, in addition to the nitrogen atom carrying the radicals R⁵ and R⁶, can additionally contain as a further hetero ring member an oxygen atom, a group $S(O)_m$ or a nitrogen atom and which can carry on ring carbon atoms one or more identical or different substituents from the group consisting of $(C_1-C_4)$-alkyl, hydroxyl and amino and can carry on a ring nitrogen atom a radical R⁷;

R⁷ is hydrogen, $(C_1-C_4)$alkyl, aryl-$(C_1-C_4)$-alkyl-, hydroxy-$(C_1-C_4)$-alkyl-, hydroxycarbonyl-$(C_1-C_4)$-alkyl-, $((C_1-C_4)$-alkoxycarbonyl)-$(C_1-C_4)$-alkyl-, $R^8R^9N$—CO—$(C_1-C_4)$-alkyl-, $R^{10}$—$SO_2$— or aryl, where R⁷, if this group is present on a piperazino radical representing $R^1R^2N$, cannot be carbocyclic aryl or carbocyclic aryl-$(C_1-C_4)$-alkyl;

R⁸ and R⁹ are identical or different radicals from the group consisting of hydrogen and $(C_1-C_4)$-alkyl;

R¹⁰ is $(C_1-C_4)$-alkyl, aryl or $R^8R^9N$;

aryl is phenyl, naphthyl or heteroaryl, which can all be substituted by one or more identical or different substituents from the group consisting of halogen, $(C_1-C_4)$-alkyl, phenyl, $CF_3$, $NO_2$, OH, —O—$(C_1-C_4)$-alkyl, —O—$(C_2-C_4)$-alkyl-O—$(C_1-C_4)$-alkyl, $(C_1-C_2)$-alkylenedioxy, $NH_2$, —NH—$(C_1-C_4)$-alkyl, —N$((C_1-C_4)$-alkyl$)_2$, —NH—CHO, —NH—CO—$(C_1-C_4)$-alkyl, —CN, —CO—$NH_2$, —CO—NH—$(C_1-C_4)$-alkyl, —CO—N$((C_1-C_4)$-alkyl$)_2$, —CO—OH, —CO—O—$(C_1-C_4)$-alkyl, —CHO and —CO—$(C_1-C_4)$-alkyl;

heteroaryl is the radical of a monocyclic 5-membered or 6-membered aromatic heterocycle or of a bicyclic 8-membered to 10-membered aromatic heterocycle, each of which contain one or more identical or different ring heteroatoms from the group consisting of N, O and S;

m is 0, 1 or 2;

in all their stereoisomeric forms and mixtures thereof in all ratios, and their physiologically tolerable salts, compounds of the formula I being excluded in which, simultaneously, R⁴ is tert-butyl or trifluoromethyl, R³ is phenyl which can be substituted by one or two identical or different substituents from the group consisting of halogen, OH, —O—$R^{11}$ and $CF_3$, $R^1R^2N$ is $R^{11}$—NH—, $(R^{11})_2N$— or $R^{12}R^{13}N$—$(CH_2)_p$—NH—, p is 2 or 3, $R^{11}$ is saturated unsubstituted $(C_1-C_4)$-alkyl and $R^{12}$ and $R^{13}$ are identical or different radicals from the group consisting of hydrogen and $R^{11}$ or the group $R^{12}R^{13}N$ is a radical, bonded via a ring nitrogen atom, of a 5-membered or 6-membered saturated heterocyclic ring which, in addition to the nitrogen atom carrying the radicals $R^{12}$ and $R^{13}$, can additionally contain as a further hetero ring member an oxygen atom, a sulfur atom or a nitrogen atom and which can be substituted by an aryl radical or by an aryl-$(C_1-C_4)$-alkyl radical, where the aryl group can be substituted by one or two identical or different substituents from the group consisting of halogen, OH, —O—$R^{11}$ and $CF_3$.

If groups or substituents can occur a number of times in the compounds of the formula I, they can all independently of one another have the indicated meanings and can each be identical or different.

Alkyl radicals can be straight-chain or branched. This also applies if they are contained in other groups, for example in alkoxy groups, alkoxycarbonyl groups or in amino groups, or if they are substituted.

Examples of alkyl groups are methyl, ethyl, propyl, butyl, pentyl, hexyl, heptyl, octyl, the n-isomers of these radicals, isopropyl, isobutyl, isopentyl, sec-butyl, tert-butyl, neopentyl, 3,3-dimethylbutyl. The term alkyl here is expressly also understood as meaning, in addition to saturated alkyl radicals, unsaturated alkyl radicals, i.e. alkyl radicals which contain one or more double bonds and/or one or more triple bonds, for example alkenyl radicals and alkynyl radicals. It will be appreciated that an unsaturated alkyl radical has to contain at least two carbon atoms, a $(C_1-C_8)$-alkyl group thus for example comprehending saturated $(C_1-C_8)$-alkyl radicals and unsaturated $(C_2-C_8)$-alkyl radicals, a $(C_1-C_4)$-alkyl radical comprehending saturated $(C_1-C_4)$-alkyl radicals and unsaturated $(C_2-C_4)$alkyl radicals. Examples of unsaturated alkyl radicals are the vinyl radical, the 2-propenyl radical (allyl radical), the 2-butenyl radical, the 2-methyl-2-propenyl radical, the ethynyl radical, the 2-propynyl radical (propargyl radical) or the 3-butynyl radical. If alkyl radicals are substituted by one or more substituents, they are preferably substituted by one, two or three, in particular by one or two, identical or different substituents. Substituents can be situated on any desired carbon atoms of the alkyl radical.

Cycloalkyl is, for example, cyclopropyl, cyclobutyl, cyclopentyl, cyclohexyl, cycloheptyl, cyclooctyl or cyclononyl, which can all also be substituted as indicated, for example by one or more identical identical or different $(C_1–C_4)$-alkyl radicals, in particular by methyl, and/or by hydroxyl. If cycloalkyl radicals are substituted by one or more substituents, they are preferably substituted by one, two, three or four, in particular by one or two, identical or different substituents. Examples of such substituted cycloalkyl radicals are 4-methylcyclohexyl, 4-tert-butylcyclohexyl, 4-hydroxycyclohexyl, 4-aminocyclohexyl or 2,3-dimethylcyclopentyl. Substituents can be situated on any desired carbon atoms of the cycloalkyl radical.

Carbocyclic aryl radicals such as phenyl radicals and naphthyl radicals and heteroaryl radicals can, if not stated otherwise, be unsubstituted or carry one or more, for example one, two, three or four, identical or different substituents, which can be situated in any desired positions. If not stated otherwise, the substituents indicated in the definition of the group aryl, for example, can occur as substituents in these radicals. If nitro groups are resent as substituents in compounds of the formula I, altogether only up to two nitro groups can be present in the molecule. If an aryl radical such as, for example, a phenyl radical in turn carries a phenyl radical as a substituent, the benzene ring in the latter can also in turn be unsubstituted or substituted by one or more, for example one, two, three or four, identical or different radicals, for example by radicals from the group consisting of $(C_1–C_4)$-alkyl, halogen, hydroxyl, $(C_1–C_4)$-alkoxy, trifluoromethyl, cyano, hydroxycarbonyl, $((C_1–C_4)$-alkoxy)carbonyl, aminocarbonyl, nitro, amino, $(C_1–C_4)$-alkylamino, di-$((C_1–C_4)$-alkyl)amino and $((C_1–C_4)$-alkyl) carbonylamino.

In monosubstituted phenyl radicals, the substituent can be situated in the 2-position, the 3-position or the 4-position, in disubstituted phenyl radicals the substituents can be situated in the 2,3-position, 2,4-position, 2,5-position, 2,6-position, 3,4-position or 3,5-position. In trisubstituted phenyl radicals, the substituents can be situated in the 2,3,4-position, 2,3,5-position, 2,3,6-position, 2,4,5-position, 2,4, 6-position or 3,4,5-position. Naphthyl can be 1-naphthyl or 2-naphthyl. In monosubstituted 1-naphthyl radicals, the substituent can be situated in the 2-position, the 3-position, the 4-position, the 5-position, the 6-position, the 7-position or the 8-position, in monosubstituted 2-naphthyl radicals in the 1-position, the 3-position, the 4-position, the 5-position, the 6-position, the 7-position or the 8-position. In polysubstituted naphthyl radicals, for example di- or trisubstituted naphthyl radicals, the substituents can also be situated in all possible positions.

If not stated otherwise, heteroaryl radicals, radicals of saturated heterocyclic rings and radicals of rings which are formed from two groups bonded to a nitrogen atom together with this nitrogen atom are preferably derived from heterocycles which contain one, two, three or four identical or different ring heteroatoms, particularly preferably from heterocycles which contain one or two or three, in particular one or two, identical or different ring heteroatoms. If not stated otherwise, the heterocycles can be monacyclic or polycyclic, for example monocyclic, bicyclic or tricyclic. Preferably, they are monocyclic or bicyclic, in particular monocyclic. The individual rings preferably contain 5, 6 or 7 ring members. Examples of monocyclic and bicyclic heterocyclic systems from which radicals occurring in the compounds of the formula I can be derived are pyrrole, furan, thiophene, imidazole, pyrazole, 1,2,3-triazole, 1,2,4-triazole, 1,3-dioxole, 1,3-oxazole, 1,2-oxazole, 1,3-hiazole, 1,2-thiazole, tetrazole, pyridine, pyridazine, pyrimidine, pyrazine, pyran, thiopyran, 1,4-dioxin, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4, 5-tetrazine, azepine, 1,2-diazepine, 1,3-diazepine, 1,4-diazepine, 1,3-oxazepine, 1,3-thiazepine, indole, benzothiophene, benzofuran, benzothiazole, benzimidazole, quinoline, isoquinoline, cinnoline, quinazoline, quinoxaline, phthalazine, thienothiophenes, 1,8-naphthyridine and other naphthyridines, pteridine, or phenothiazine, all in each case in saturated form (perhydro form) or in partially unsaturated form (for example dihydro form and tetrahydro form) or in maximally unsaturated form, if the forms concerned are known and stable. The heterocycles which are suitable also include, for example, the saturated heterocycles pyrrolidine, piperidine, perhydroazepine (hexamethyleneimine), piperazine, morpholine, 1,3-thiazolidine and thiomorpholine. The degree of saturation of heterocyclic groups is indicated in the individual definitions. Unsaturated heterocycles can, for example, contain one, two or three double bonds in the ring system, 5-membered rings and 6-membered rings in monocyclic and polycyclic heterocycles can, in particular, also be aromatic.

Heterocyclic radicals can be bonded via any suitable ring carbon atom. Nitrogen heterocycles, for example pyrrole, imidazole, pyrrolidine, piperidine, hexamethyleneimine, 1,3-thiazolidine, morpholine, thiomorpholine, piperazine etc., can also be bonded via any suitable ring nitrogen atom, in particular if the nitrogen heterocycle concerned is bonded to a carbon atom. For example, a thienyl radical can be present as a 2-thienyl radical or 3-thienyl radical, a furan radical as a 2-furyl radical or 3-furyl radical, a pyridyl radical as a 2-pyridyl radical, 3-pyridyl radical or 4-pyridyl radical, a piperidine radical as a 1-piperidinyl radical (=piperidino radical), 2-piperidinyl radical, 3-piperidinyl radical or 4-piperidinyl radical, a (thio)morpholine radical as a 2-(thio)morpholinyl radical, 3-(thio)morpholinyl radical or 4-(thio)morpholinyl radical (=(thio)morpholino radical). A radical which is derived from 1,3-thiazole can be bonded via the 2-position, the 3-position, the 4-position or the 5-position, a radical which is derived from imidazole can be bonded via the 1-position, the 2-position, the 4-position or the 5-position.

If not stated otherwise, the heterocyclic groups can be unsubstituted or can carry one or more, for example one, two, three or four identical or different substituents. The substituents in heterocycles can be situated in any desired positions, for example in a 2-thienyl radical or 2-furyl radical in the 3-position and/or in the 4-position and/or in the 5-position, in a 3-thienyl radical or 3-furyl radical in the 2-position and/or in the 4-position and/or in the 5-position, in a 2-pyridyl radical in the 3-position and/or in the 4-position and/or in the 5-position and/or in the 6-position, in a 3-pyridyl radical in the 2-position and/or in the 4-position and/or in the 5-position and/or in the 6-position, in a 4-pyridyl radical in the 2-position and/or in the 3-position and/or in the 5-position and/or in the 6-position. If not stated otherwise, the substituents which can occur are, for example, the substituents indicated in the definition of the group aryl, in the case of saturated or partially unsaturated heterocycles as further substituents also the oxo group and the thioxo group. Substituents on a heterocycle and also substituents on a carbocycle can also form a ring, further rings can thus be fused to a ring system such that, for example, cyclopenta-fused, cyclohexa-fused or benzo-fused rings can be present. If not stated otherwise, possible substituents on a substitutable nitrogen atom of a heterocycle are, for example, unsubstituted and substituted $(C_1-C_4)$-alkyl radicals, aryl radicals, acyl radicals such as —CO—$(C_1-C_4)$-alkyl or —CO-aryl, or sulfonyl radicals such as —$SO_2$—$(C_1-C_4)$-alkyl or —$SO_2$-aryl. Suitable sulfur heterocycles can also be present as S-oxides or S,S-dioxides, i.e. they can contain the group $S(=O)$ or the group $S(=O)_2$ instead of a sulfur atom. Suitable nitrogen heterocycles can also be present as N-oxides or as quaternary salts with an anion derived from a physiologically tolerable acid as a counterion. Pyridyl radicals can be present, for example, as pyridine N-oxides.

Halogen is fluorine, chlorine, bromine or iodine, preferably fluorine or chlorine.

The present invention includes all stereoisomeric forms of the compounds of the formula I. Asymmetric centers contained in the compounds of the formula I can all independently of one another have the S configuration or the R configuration. The invention includes all possible enantiomers and diastereomers, as well as mixtures of two or more stereoisomeric forms, for example mixtures of enantiomers and/or diastereomers, in all ratios. The invention thus relates to enantiomers in enantiomerically pure form, both as levorotatory and as dextrorotatory antipodes, in the form of racemates and in the form of mixtures of the two enantiomers in all ratios. In the presence of cis/trans isomerism, for example on double bonds or cycloalkyl groups, the invention relates both to the cis form and the trans form and mixtures of these forms in all ratios. Individual stereoisomers can be prepared, if desired, by resolution of a mixture by customary methods, for example by chromatography or crystallization, by use of stereochemically homogeneous starting substances in the synthesis or by stereoselective synthesis. If appropriate, derivatization can be carried out before separation of stereoisomers. The separation of a stereoisomer mixture can be carried out at the stage of the compounds of the formula I or at the stage of an intermediate in the course of the synthesis. If mobile hydrogen atoms are present, the present invention also includes all tautomeric forms of the compounds of the formula I.

If the compounds of the formula I contain one or more acidic or basic groups, the invention also relates to the corresponding physiologically or toxicologically tolerable salts, in particular the pharmaceutically utilizable salts. Thus the compounds of the formula I which contain acidic groups, can be present on these groups, and can be used according to the invention, for example as alkali metal salts, alkaline earth metal salts or as ammonium salts. Examples of such salts are sodium salts, potassium salts, calcium salts, magnesium salts or salts with ammonia or organic amines, for example ethylamine, ethanolamine, triethanolamine or amino acids. Compounds of the formula I which contain one or more basic, i.e. protonatable, groups can be present, and can be used according to the invention, in the form of their acid addition salts with physiologically tolerable inorganic or organic acids, for example as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid etc. If the compounds of the formula I simultaneously contain acidic and basic groups in the molecule, in addition to the salt forms outlined the invention also includes internal salts or betaines (zwifterions). Salts can be obtained from the compounds of the formula I by customary processes known to the person skilled in the art, for example by combination with an organic or inorganic acid or base in a solvent or dispersant, or alternatively from other salts by anion exchange or cation exchange. The present invention also includes all salts of the compounds of the formula I which, because of low physiological tolerability, are not directly suitable for use in pharmaceuticals, but are suitable, for example, as intermediates for chemical reactions or for the preparation of physiologically tolerable salts.

The present invention furthermore includes all solvates of compounds of the formula I, for example hydrates or adducts with alcohols, and also derivatives of the compounds of the formula I such as, for example, esters and amides, and prodrugs and active metabolites.

Preferably, $R^1$ is $(C_1-C_8)$-alkyl which can be substituted by one or more identical or different substituents from the group consisting of hydroxyl, $(C_1-C_4)$-alkoxy, $(C_1-C_4)$-alkyl—$S(O)_m$—, $R^5R^6N$ and aryl, or $(C_3-C_9)$—cycloalkyl which can be substituted by one or more identical or different substituents from the group consisting of $(C_1-C_4)$-alkyl, hydroxyl and amino. Preferably, $R^2$ is hydrogen, $(C_1-C_8)$-alkyl which can be substituted by one or more identical or different substituents from the group consisting of hydroxyl, $(C_1-C_4)$-alkoxy, $(C_1-C_4)$-alkyl-$S(O)_m$—, $R^5R^6N$ and aryl, or $(C_3-C_9)$-cycloalkyl which can be substituted by one or more identical or different substituents from the group consisting of $(C_1-C_4)$-alkyl, hydroxyl and amino. It is particularly preferred if $R^1$ is $(C_1-C_8)$-alkyl or $(C_3-C_9)$-cycloalkyl and $R^2$ is hydrogen or if $R^1$ and $R^2$ are identical or different $(C_1-C_8)$-alkyl, where all radicals can be unsubstituted or substituted as indicated. It is very particularly preferred if $R^1$ is $(C_3-C_9)$-cycloalkyl which can be substituted by one or more identical or different substituents from the group consisting of $(C_1-C_4)$-alkyl, hydroxyl and amino, and $R^2$ is hydrogen. If $R^1$ is $(C_3-C_9)$-cycloalkyl which can be substituted by one or more identical or different substituents from the group consisting of $(C_1-C_4)$-alkyl, hydroxyl and amino, or the radical of a 5-membered, 6-membered or 7-membered saturated heterocyclic ring which contains one or two identical or different hetero ring members from the group consisting of O, $NR^7$ and $S(O)_m$ and which can be substituted by one or more identical or different substituents from the group consisting of $(C_1-C_4)$-alkyl and aryl-$(C_1-C_4)$-alkyl-, then $R^2$ is preferably hydrogen. An alkyl radical representing $R^1$ or $R^2$ is preferably an unsubstituted or substituted $(C_1-C_4)$-alkyl radical. A $(C_3-C_9)$-cycloalkyl radical representing $R^1$ or $R^2$ is preferably an unsubstituted or substituted $(C_3-C_7)$-cycloalkyl radical.

In addition to the abovementioned preferred meanings of $R^1$ and $R^2$, it is furthermore preferred if the group $R^1R^2N$ is a radical, bonded via a ring nitrogen atom, of a 5-membered, 6-membered or 7-membered saturated heterocyclic ring which, in addition to the nitrogen atom carrying the radicals $R^1$ and $R^2$, can additionally contain as a further hetero ring member an oxygen atom, a group $S(O)_m$ or a nitrogen atom carrying a radical $R^7$ and which can be substituted by one or more identical or different substituents from the group consisting of $(C_1-C_4)$-alkyl, hydroxyl, $(C_1-C_4)$-alkoxy, $R^8R^9N$, hydroxycarbonyl, $(C_1-C_4)$-alkoxycarbonyl and $R^8R^9N$—CO—. A radical representing $R^1R^2N$ of a heterocyclic ring is preferably derived from a 5-membered or 6-membered saturated heterocyclic ring, particularly preferably from piperidine, morpholine, thiomorpholine (and its S-oxide and S, S-dioxide) or piperazine, which can all be substituted as indicated, very particularly preferably from unsubstituted piperidine, morpholine or thiomorpholine (and its S-oxide and S,S-dioxide) or from N-methylpiperazine.

The aryl group representing $R^3$ is preferably unsubstituted or substituted phenyl, particularly preferably substituted phenyl, very particularly preferably phenyl, which is substituted by one or two substituents from those indicated above for aryl. Especially preferably, $R^3$ is phenyl which is substituted by one or two identical or different substituents from the group consisting of halogen and $(C_1-C_4)$-alkyl, moreover preferably phenyl which is substituted by chlorine or methyl. The substituent in a monosubstituted phenyl group representing $R^3$ is preferably in the para-position.

$R^4$ is preferably $(C_2-C_5)$-alkyl, trifluoromethyl or unsubstituted or substituted phenyl, particularly preferably straight-chain or branched $(C_3-C_4)$-alkyl, for example n-propyl, isopropyl, n-butyl, isobutyl or tert-butyl.

Aryl is preferably phenyl or 5-membered or 6-membered monocyclic heteroaryl having one or two, in particular one, heteroatom from the group consisting of N, O and S, which can be substituted as indicated, particularly preferably unsubstituted or substituted phenyl or unsubstituted pyridyl, thienyl or furyl, very particularly preferably unsubstituted or substituted phenyl or unsubstituted pyridyl.

Preferred compounds of the formula I are those in which one or more of the radicals contained therein have preferred meanings, the present invention relating to all combinations of preferred substituent definitions. The present invention also includes, of all preferred compounds of the formula I, all their stereoisomeric forms and mixtures thereof in all ratios, and their physiologically tolerable salts.

The present invention also relates to processes for the preparation of the compounds of the formula I, which are explained below and by which the compounds according to the invention are obtainable. The compounds of the formula I can be prepared by first reacting an amidine of the formula II in a manner known per se with a 3-oxopropionic acid ester of the formula III carrying a radical $R^4$ in the 3-position to give a 4-hydroxypyrimidine of the formula IV. R in the formula III is, for example, $(C_1-C_4)$-alkyl such as methyl or ethyl. The hydroxypyrimidine of the formula IV is then activated, for example by conversion into a 4-halopyrimidine. For example, the compound of the formula IV can be converted into the 4-chloropyrimidine of the formula V by reaction with a phosphorus halide such as phosphorus oxychloride. By reaction of the compound of the formula V (or of another reactive derivative of the hydroxypyrimidine) with the desired amine of the formula VI, the compound of the formula I according to the invention is then obtained with replacement of the chlorine by the amino group. Suitable solvents for this replacement reaction are, for example, water, alcohols such as methanol, ethanol or isopropanol, ethers such as tetrahydrofuran or dioxane, amides such as dimethylformamide (DMF) or N-methylpyrrolidone (NMP), or hydrocarbons or halogenated hydrocarbons such as benzene, toluene, xylene, chlorobenzene or dichlorobenzene.

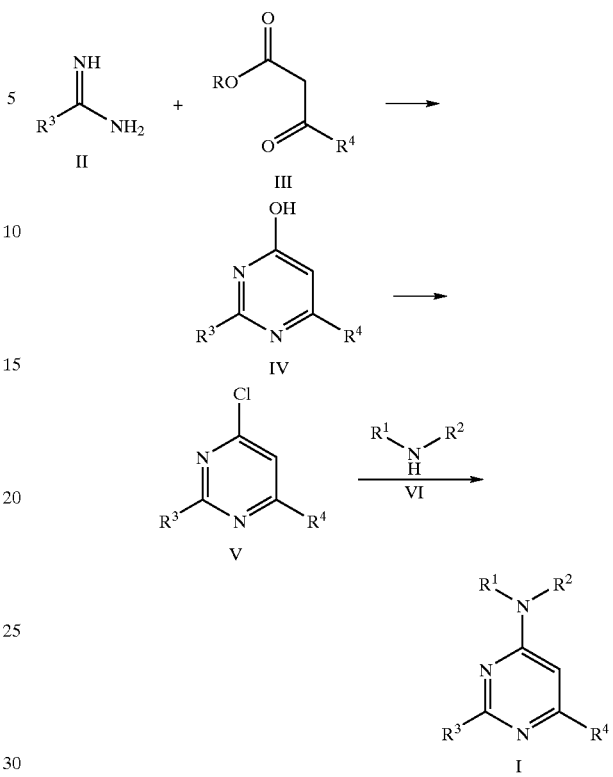

The reactions for the synthesis of the compounds of the formula I can be carried out in a wide temperature range. Reaction temperatures of 20° C. to 150° C. are preferred. The reactions can be accelerated by addition of suitable bases such as, for example, sodium bicarbonate, sodium carbonate, potassium carbonate, sodium alkoxides, triethylamine or pyridine, in the first and in the last step additionally also by an excess of amidine of the formula II or amine of the formula VI. Instead of the free amidines of the formula II, the corresponding amidinium salts can also be employed. In this case, it is particularly convenient to carry out the first step with addition of bases. The intermediates of the formula IV and V and the final compounds of the formula I can be separated from the respective reaction mixture by customary processes such as crystallization, sublimation, chromatography or distillation and, if desired, purified, however, depending on the circumstances of the individual case, the intermediates can be reacted further also without intermediate isolation. Moreover, functional groups in the compounds obtained can be converted.

For example, thioether groups can be converted into sulfones or sulfoxides by oxidation with a peroxy compound such as 3-chloroperbenzoic acid or monoperoxyphthalic acid or hydrogen peroxide, or carboxylic acid ester groups can be hydrolyzed to the carboxylic acids.

All reactions for the synthesis of the compounds of the formula I are well known per se to the person skilled in the art and can be carried out under standard conditions according to or analogously to literature procedures, such as are described, for example, in Houben-Weyl, Methoden der Organischen Chemie [Methods of Organic Chemistry], Thieme-Verlag, Stuttgart, or Organic Reactions, John Wiley & Sons, New York. Depending on the conditions of the individual case, it may also be advantageous or necessary for the avoidance of side reactions in the synthesis of the compounds of the formula I to temporarily block certain functional groups by the introduction of protective groups and then later to liberate them again or to employ functional groups first in the form of precursors, from which the desired functional group is then produced in a later step. Such synthesis strategies and the protective groups or precursors suitable for the individual case are known to the person skilled in the art. The starting amidines of the formula II or their salts, the oxoesters of the formula III and the amines of the formula VI are commercially obtainable or can be prepared by or analogously to known processes.

The compounds of the formula I according to the invention bring about an increase in the cGMP concentration by means of the activation of soluble guanylate cyclase (sGC) and are therefore valuable agents for the therapy and prophylaxis of illnesses which are associated with a low or reduced cGMP level or are caused by such a level or for whose therapy or prophylaxis an increase in the cGMP level present is desired. The activation of sGC by the compounds of the formula I can be investigated, for example, in the activity assay described below.

Illnesses and pathological conditions which are associated with a low cGMP level or in which an increase in the cGMP level is desired and for whose therapy and prophylaxis compounds of the formula I can be employed are, for example, cardiovascular disorders such as endothelial dysfunction, diastolic dysfunction, atherosclerosis, high blood pressure, stable and unstable angina pectoris, thromboses, restenoses, myocardial infarcts, strokes, cardiac insufficiency or pulmonary hypertension, or, for example, erectile dysfunction, bronchial asthma, chronic renal insufficiency and diabetes. Compounds of the formula I can more over be employed in the therapy of liver cirrhosis and for improving restricted learning capacity or memory power.

The compounds of the formula I and their physiologically tolerable salts can thus be used in animals, preferably in mammals, and in particular in humans, as pharmaceuticals on their own, in mixtures with one another or in the form of pharmaceutical preparations. The present invention therefore also relates to the compounds of the formula I and their physiologically tolerable salts for use as pharmaceuticals, their use for the normalization of a disturbed cGMP balance and in particular their use in the therapy and prophylaxis of the abovementioned syndromes, and their use for the production of medicaments therefor. The present invention furthermore relates to pharmaceutical preparations (or pharmaceutical compositions) which contain an efficacious dose of at least one compound of the formula I and/or of a physiologically tolerable salt thereof as an active constituent and a pharmaceutically tolerable carrier, i.e. one or more customary pharmaceutically tolerable vehicles and/or excipients (or additives).

The pharmaceuticals according to the invention can be administered orally, for example in the form of pills, tablets, film-coated tablets, coated tablets, granules, hard and soft gelatin capsules, aqueous, alcoholic or oily solutions, syrups, emulsions or suspensions, or rectally, for example in the form of suppositories. Administration, however, can also be carried out parenterally, for example subcutaneously, intramuscularly or intravenously in the form of injection solutions or infusion solutions. Further possible administration forms are, for example, percutaneous or topical application, for example in the form of ointments, tinctures, sprays or transdermal therapeutic systems, or administration by inhalation in the form of nasal sprays or aerosol mixtures, or, for example, microcapsules, implants or rods. The preferred administration form depends, for example, on the illness to be treated and its severity.

The pharmaceutical preparations normally contain 0.2 to 500 mg, preferably 1 to 200 mg, of active compound of the formula I and/or its physiologically tolerable salts; depending on the nature of the preparation and the intended use the amount of the active compound contained can also be larger. The pharmaceutical preparations can be produced in a manner known per se. For this, one or more compounds of the formula I and/or their physiologically tolerable salts are brought, together with one or more solid or liquid pharmaceutical vehicles and/or additives and, if desired, in combination with other pharmaceutical active compounds having therapeutic or prophylactic action, into a suitable administration form or dose form, which can then be used as a pharmaceutical in human or veterinary medicine. The pharmaceutical preparations normally contain 0.5 to 90 percent by weight of the compounds of the formula I and/or their physiologically tolerable salts.

For the production, for example, of pills, tablets, coated tablets and hard gelatin capsules, it is possible to use lactose, starch, for example corn starch, or starch derivatives, talc, stearic acid or its salts, etc. Vehicles for soft gelatin capsules and suppositories are, for example, fats, waxes, semisolid and liquid polyols, natural or hardened oils etc. Suitable vehicles for the preparation of solutions, for example injection solutions, or of emulsions or syrups are, for example, water, physiological saline solution, alcohols such as ethanol, glycerol, polyols, sucrose, invert sugar, glucose, mannitol, vegetable oils etc. The compounds of the formula I and their physiologically tolerable salts can also be lyophilized and the lyophilizates obtained used, for example, for the production of injection preparations or infusion preparations. Suitable vehicles for microcapsules, implants or rods are, for example, copolymers of glycolic acid and lactic acid.

In addition to the active compounds and vehicles, the pharmaceutical preparations can additionally contain customary excipients or additives, for example fillers, disintegrants, binders, lubricants, wetting agents, stabilizers, emulsifiers, dispersants, preservatives, sweetening agents, colorants, flavorings, aromatizers, thickening agents, diluents, buffer substances, solvents, solubilizers, agents for achieving a depot effect, salts for altering the osmotic pressure, coating agents or antioxidants.

The dose of the active compound of the formula I to be administered and/or of one of its physiologically tolerable salts depends on the individual case and is to be suited to the individual conditions as customary for an optimal action. Thus it depends on the nature and severity of the illness to be treated, on the sex, age, weight and individual responsiveness of the human or animal to be treated, on the potency and duration of action of the compounds employed, on whether the therapy is acute or chronic or prophylaxis is carried out, or on whether further active compounds are administered in addition to compounds of the formula I. In general, a daily dose of approximately 0.01 to 100 mg/kg, preferably 0.1 to 10 mg/kg, in particular 0.3 to 5 mg/kg (in each case mg per kg of body weight) is appropriate in the case of administration to an adult of about 75 kg in weight to achieve the desired action. The daily dose can be administered in a single dose or, in particular in the case of administration of relatively large amounts, divided into a number of, for example two, three or four, individual doses. If appropriate, depending on individual behavior, it may be necessary to deviate upward or downward from the daily dose indicated.

The compounds of the formula I activate the soluble guanylate cyclase. On account of this property, apart from as pharmaceutical active compounds in human medicine and veterinary medicine, they can also be used as a scientific tool or as an aid for biochemical investigations in which an effect on guanylate cyclase of this type is intended, and also for diagnostic properties, for example in the in vitro diagnosis of cell or tissue samples. In addition, the compounds of the formula I and their salts, as already mentioned above, can serve as intermediates for the preparation of further pharmaceutical active compounds.

The following examples illustrate the invention without restricting it.

EXAMPLES

Example 1
2-(4-Chlorophenyl)-4-hydroxy-6-isopropylpyrimidine

A mixture of 19.1 g of 4-chlorobenzamidine hydrochloride, 15.8 g of ethyl 4-methyl-3-oxopentanoate, 11.2 g of potassium tert-butoxide and 200 ml of ethanol was heated under reflux for 2 hours. After cooling to room temperature, the solid was filtered off with suction, washed with water and with a little ethanol and dried at 40° C. in vacuo. Yield: 12.5 g. M.p.: 164° C.

The following were prepared analogously:

Example 2
2-(4-Chlorophenyl)4-hydroxy-6-trifluoromethylpyrimidine; m.p.: 258° C.

Example 3
2-(4-Chlorophenyl)6-tert-butyl-4-hydroxypyrimidine; m.p.: 193° C.

Example 4
2-(4-Chlorophenyl)4-hydroxy-6-phenylpyrimidine; m.p.: 306° C.

Example 5
2-(4-Methylphenyl)4-hydroxy-6-isopropylpyrimidine; m.p.: 164° C.

Example 6
2-(3,5-Dichlorophenyl)4-hydroxy-6-isopropylpyrimidine; m.p.: 203° C.

Example 7
2-(4-Aminocarbonylphenyl)-4-hydroxy-6-isopropylpyrimidine; m.p.: 294° C.

Example 8
4-Chloro-2-(4-chlorophenyl)-6isopropylpyrimidine

The mixture of 12 g of 2-(4-chlorophenyl)-4-hydroxy-6-isopropylpyrimidine and 35 ml of phosphorus oxychloride was heated at 90° C. for 3 hours with stirring. Most of the excess of the phosphorus oxychloride was distilled off in vacuo, and the residue was added to 100 ml of ice water and stirred. The solid white precipitate forming was filtered off with suction and dried in vacuo at room temperature.
Yield: 11.4 g
M.p.: 74° C.

The following were prepared analogously:

Example 9
4-Chloro-2-(4-chlorophenyl)6-trifluoromethylpyrimidine; m.p.: 76° C.

Example 10
4-Chloro-2-(4-chlorophenyl)6-tert-butylpyrimidine; m.p.: 93° C.

Example 11
4-Chloro-2-(4-chlorophenyl)-6-phenylpyrimidine; m.p.: 127° C.

Example 12
4-Chloro-2-(4-methylphenyl)6-isopropylpyrimidine; m.p.: oil

Example 13
4-Chloro-2-(3,5-dichlorophenyl)-6-isopropylpyrimidine; m.p.: 59° C.

Example 14
4-Chloro-2-(4-cyanophenyl)-6-isopropylpyrimidine of m.p. 114° C. was obtained in an analogous reaction starting from 2-(4-aminocarbonylphenyl)-4-hydroxy-6-isopropylpyrimidine.

Example 15
2-(4-Chlorophenyl)-6isopropyl-4-((2,2,6,6-tetramethylpiperidin-4-yl)amino)-pyrimidine dihydrochloride A mixture of 534 mg of 4-chloro-2-(4-chlorophenyl)-6-isopropylpyrimidine and 1.8 g of 4-amino-2,2,6,6-tetramethylpiperidine was heated at 150° C. for 2 hours with stirring. After cooling, 20 ml of water were added and the mixture was stirred at room temperature. The white precipitate was filtered off with suction, dried in vacuo and taken up in 20 ml of ethyl acetate. By addition of hydrogen chloride, the title compound was precipitated, filtered off with suction and dried in vacuo. Yield: 0.8 g.
M.p.: 359° C.

Example 16
2-(4-Chlorophenyl)-6-isopropyl-4-morpholinopyrimidine

A mixture of 267 mg of 4-chloro-2-(4-chlorophenyl)-6-isopropylpyrimidine and 522 mg of morpholine was heated at 130° C. for 2 hours. After cooling, 20 ml of water were added, the mixture was stirred, and the solid was filtered off with suction and dried at 50° C. in vacuo. Yield: 0.28 g.
M.p.: 123° C.

The following compounds of the formula I were prepared analogously to Examples 15 and 16. If an acid is specified in the column "M.p.", the compound was obtained in the form of the acid addition salt with the specified acid. The specification "2HCl" means that the compound was obtained as a dihydrochloride.

| Ex. No. | $R^4$ | $R^3$ | $R^1R^2N$ | M.p. (° C.) |
|---|---|---|---|---|
| 17 | $CF_3$ | 4-Chlorophenyl | (3-Phenylpropyl)amino | Oil |
| 18 | $CF_3$ | 4-Chlorophenyl | (2-Ethylthioethyl)amino | 114 (HCl) |
| 19 | $CF_3$ | 4-Chlorophenyl | (1-Benzylpiperidin-4-yl)amino | 128 (2HCl) |
| 20 | $CF_3$ | 4-Chlorophenyl | 4-(2-Hydroxyethyl)-piperazino | 119 |
| 21 | Isopropyl | 2-Pyridyl | Benzylamino | 150 |
| 22 | Isopropyl | 2-Pyrazinyl | Thiomorpholino | 107 |
| 23 | Isopropyl | 4-Methylphenyl | (3-Methoxypropyl)amino | Oil |
| 24 | Isopropyl | 4-Methylphenyl | Cyclopentylamino | 66 |
| 25 | Isopropyl | 4-Methylphenyl | (trans-4-Hydroxycyclohexyl)amino | Oil |
| 26 | Isopropyl | 4-Chlorophenyl | (3-Methoxypropyl)amino | Oil |
| 27 | Isopropyl | 4-Chlorophenyl | 4-Methylpiperazino | 292 (2HCl) |

-continued

| Ex. No. | R⁴ | R³ | R¹R²N | M.p. (°C.) |
|---|---|---|---|---|
| 28 | Isopropyl | 4-Chlorophenyl | Piperidino | 75 |
| 29 | Isopropyl | 4-Chlorophenyl | Pyrrolidino | 215 (HCl) |
| 30 | Isopropyl | 4-Chlorophenyl | Thiomorpholino | 215 (HCl) |
| 31 | Isopropyl | 4-Chlorophenyl | (2-(3-Methoxyphenyl)ethyl)amino | 213 (HCl) |
| 32 | Isopropyl | 4-Chlorophenyl | Butylamino | Oil |
| 33 | Isopropyl | 4-Chlorophenyl | Diethylamino | Oil |
| 34 | Isopropyl | 4-Chlorophenyl | Dibutylamino | 165 (HCl) |
| 35 | Isopropyl | 4-Chlorophenyl | Dipropylamino | 176 (HCl) |
| 36 | Isopropyl | 4-Chlorophenyl | Diallylamino | 118 |
| 37 | Isopropyl | 4-Chlorophenyl | Di(2-methoxyethyl)amino | 127 |
| 38 | Isopropyl | 4-Chlorophenyl | Perhydroazepin-1-yl | 68 |
| 39 | Isopropyl | 4-Chlorophenyl | Benzylamino | 108 |
| 40 | Isopropyl | 4-Chlorophenyl | (2-Methoxyethyl)amino | 152 (HCl) |
| 41 | Isopropyl | 4-Chlorophenyl | (2-Ethylmercaptoethyl)amino | 148 (HCl) |
| 42 | Isopropyl | 4-Chlorophenyl | (3-Morpholinopropyl)amino | 245 (2HCl) |
| 43 | Isopropyl | 4-Chlorophenyl | N-(Ethyl)-N-(benzyl)amino | Oil |
| 44 | Isopropyl | 4-Chlorophenyl | 4-Aminocarbonyl-piperidino | 189 |
| 45 | Isopropyl | 4-Chlorophenyl | 1,3-Thiazolidin-3-yl | 77 |
| 46 | Isopropyl | 4-Chlorophenyl | 4-(Dimethylamino-sulfonyl)piperazino | 150 |
| 47 | Isopropyl | 4-Chlorophenyl | 4-Benzylpiperazino | 265 (2HCl) |
| 48 | Isopropyl | 4-Chlorophenyl | 4-((Isopropylamino-carbonyl)methyl)piperazino | 133 |
| 49 | tert-Butyl | 4-Chlorophenyl | 4-Methylpiperazino | 122 |
| 50 | tert-Butyl | 4-Chlorophenyl | (2-Methoxyethyl)amino | 94 |
| 51 | tert-Butyl | 4-Chlorophenyl | (3-Pyridylmethyl)amino | 143 |
| 52 | tert-Butyl | 4-Chlorophenyl | Morpholino | 136 |
| 53 | tert-Butyl | 4-Chlorophenyl | 4-(Dimethylaminosulfonyl)piperazino | 168 |
| 54 | tert-Butyl | 4-Chlorophenyl | (2,2,6,6-Tetramethyl-piperidin-4-yl)amino | 142 |
| 55 | Phenyl | 4-Chlorophenyl | Morpholino | 193 |
| 56 | Phenyl | 4-Chlorophenyl | 4-Methylpiperazino | 167 |
| 57 | Phenyl | 4-Chlorophenyl | (3-Pyridylmethyl)amino | 130 |
| 58 | Phenyl | 4-Chlorophenyl | (3-(Imidazol-1-yl)propyl)amino | 154 |
| 59 | Phenyl | 4-Chlorophenyl | (2-(3-Methoxyphenyl)ethyl)amino | 103 (HCl) |
| 60 | Phenyl | 4-Chlorophenyl | 4-Carboxy-1,3-thiazolidin-3-yl | 113 |
| 61 | Isopropyl | 2-Thienyl | Pyrrolidino | 74 |
| 62 | Isopropyl | 2-Thienyl | cis-2,6-Dimethyl-morpholino | 103 |
| 63 | Phenyl | 4-Chlorophenyl | Diethylamino | 132 |
| 64 | Phenyl | 4-Chlorophenyl | Butylamino | 95 (HCl) |
| 65 | Phenyl | 4-Chlorophenyl | Thiomorpholino | 175 |
| 66 | tert-Butyl | 4-Chlorophenyl | Thiomorpholino | 119 |
| 67 | Isopropyl | 4-Pyridyl | Butylamino | 101 |
| 68 | Isopropyl | 4-Pyridyl | (3-Phenylpropyl)amino | Resin |
| 69 | Phenyl | 4-Chlorophenyl | Dipropylamino | 72 |
| 70 | Isopropyl | 4-Chlorophenyl | Cyclopropylamino | Oil |
| 71 | CF₃ | 4-Chlorophenyl | (3-Pyridylmethyl)amino | 181 |
| 72 | Isopropyl | 4-Chlorophenyl | 3,3-Dimethylpiperidino | Oil |
| 73 | CF₃ | 4-Chlorophenyl | 4-Methylpiperazino | 108 |
| 74 | CF₃ | 4-Chlorophenyl | Morpholino | 184 |
| 75 | tert-Butyl | 4-Chlorophenyl | Perhydroazepin-1-yl | 151 |
| 76 | tert-Butyl | 4-Chlorophenyl | 4-Aminocarbonyl-piperidino | 164 |
| 77 | Isopropyl | 3,5-Dichlorophenyl | (trans-4-Hydroxy-cyclohexyl)amino | 174 |
| 78 | Isopropyl | 3,5-Dichlorophenyl | (2-Hydroxyethyl)amino | 88 |
| 79 | Isopropyl | 3,5-Dichlorophenyl | Butylamino | 190 (HCl) |
| 80 | Isopropyl | 3,5-Dichlorophenyl | Diethylamino | Oil |
| 81 | Isopropyl | 3,5-Dichlorophenyl | Morpholino | 138 |
| 82 | Isopropyl | 3,5-Dichlorophenyl | Thiomorpholino | 130 |
| 83 | Isopropyl | 3,5-Dichlorophenyl | 4-Methylpiperazino | 123 |
| 84 | Isopropyl | 3,5-Dichlorophenyl | Dipropylamino | Oil |
| 85 | Isopropyl | 4-Methylphenyl | Dipropylamino | Oil |
| 86 | Isopropyl | 4-Methylphenyl | Diethylamino | 180 (HCl) |
| 87 | Isopropyl | 4-Methylphenyl | (3-Hydroxypropyl)amino | 86 |
| 88 | Isopropyl | 4-Methylphenyl | Butylamino | Oil |
| 89 | Isopropyl | 4-Methylphenyl | Morpholino | 95 |
| 90 | Isopropyl | 4-Methylphenyl | Thiomorpholino | 107 |
| 91 | Isopropyl | 4-Methylphenyl | 4-Methylpiperazino | 70 |
| 92 | Isopropyl | 4-Chlorophenyl | N-(Ethyl)-N-(butyl)amino | Oil |
| 93 | Isopropyl | 4-Chlorophenyl | N-(Methyl)-N-(butyl)amino | Oil |
| 94 | Isopropyl | 4-Chlorophenyl | 4-(2-Pyridyl)piperazino | 166 |
| 95 | CF₃ | 4-Chlorophenyl | 4-(2-Pyridyl)piperazino | 174 |
| 96 | Isopropyl | 4-Chlorophenyl | cis/trans-2,6-Dimethyl-morpholino | Oil |
| 97 | Isopropyl | 4-Methylphenyl | cis-2,6-Dimethyl-morpholino | Oil |
| 98 | Isopropyl | 4-Methylphenyl | Di(2-methoxyethyl)amino | Oil |
| 99 | Isopropyl | 4-Methylphenyl | 4-Aminocarbonyl-piperidino | 192 |
| 100 | Isopropyl | 4-Methylphenyl | Perhydroazepin-1-yl | Oil |
| 101 | tert-Butyl | 4-Chlorophenyl | cis-2,6-Dimethyl-morpholino | 117 |
| 102 | tert-Butyl | 4-Chlorophenyl | (3-Methoxypropyl)amino | Oil |
| 103 | tert-Butyl | 4-Chlorophenyl | Di(2-methoxyethyl)amino | Oil |
| 104 | Isopropyl | 4-Chlorophenyl | cis-2,6-Dimethyl-morpholino | 114 |
| 105 | Isopropyl | 4-Chlorophenyl | (2-Diisopropylamino-ethyl)amino | 219 (2HCl) |
| 106 | Isopropyl | 4-Chlorophenyl | 4-(2-Hydroxyethyl)piperazino | 227 (2HCl) |
| 107 | Isopropyl | 4-Chlorophenyl | (1-Benzylpiperidin-4-yl)amino | 250 (2HCl) |
| 108 | Phenyl | 4-Chlorophenyl | cis/trans-2,6-Dimethyl-morpholino | 187 |
| 109 | Phenyl | 4-Chlorophenyl | (3-Methoxypropyl)amino | Oil |
| 110 | Phenyl | 4-Chlorophenyl | Di(2-methoxyethyl)amino | Oil |
| 111 | Phenyl | 4-Chlorophenyl | 4-Aminocarbonyl-piperidino | 204 |
| 112 | Phenyl | 4-Chlorophenyl | Perhydroazepin-1-yl | 126 |
| 113 | Isopropyl | 4-Cyanophenyl | (4-Hydroxybutyl)amino | 93 |
| 114 | Isopropyl | 4-Cyanophenyl | (3-Methoxypropyl)amino | 70 |
| 115 | Isopropyl | 4-Cyanophenyl | Butylamino | 89 |
| 116 | Isopropyl | 4-Cyanophenyl | Cyclopentylamino | 141 |
| 117 | Isopropyl | 4-Cyanophenyl | (4-Hydroxycyclohexyl)amino | 101 |
| 118 | Isopropyl | 4-Cyanophenyl | (3-Pyridylmethyl)amino | 149 |
| 119 | Isopropyl | 4-Cyanophenyl | Dipropylamino | 80 |
| 120 | Isopropyl | 4-Cyanophenyl | Perhydroazepin-1-yl | 117 |
| 121 | Isopropyl | 4-Cyanophenyl | Morpholino | 224 |
| 122 | Isopropyl | 4-Cyanophenyl | 4-Methylpiperazino | 152 |
| 123 | Isopropyl | 2-Methylthiazol-4-yl | Dipropylamino | Oil |
| 124 | Isopropyl | 4-Chlorophenyl | Cyclopentylamino | 82 |
| 125 | Isopropyl | 4-Chlorophenyl | (trans-4-Hydroxycyclohexyl)amino | 138 |
| 126 | Isopropyl | 4-Chlorophenyl | (trans-4-Aminocyclohexyl)amino | 128 |
| 127 | Isopropyl | 4-Chlorophenyl | (cis/trans-4-Hydroxy-cyclohexyl)amino | Oil |

-continued

| Ex. No. | R⁴ | R³ | R¹R²N | M.p. (° C.) |
|---|---|---|---|---|
| 128 | Isopropyl | 4-Chlorophenyl | (4-Methylcyclohexyl)-amino | Oil |
| 129 | Isopropyl | 4-Chlorophenyl | N-(Cyclohexyl)-N-(methyl)amino | 88 |
| 130 | Isopropyl | 4-Chlorophenyl | (2-Isopropyl-5-methylcyclohexyl)amino | Oil |
| 131 | Isopropyl | 4-Chlorophenyl | (trans-2-Hydroxycyclohexyl)amino | Oil |
| 132 | tert-Butyl | 4-Chlorophenyl | Cyclopentylamino | 89 |
| 133 | tert-Butyl | 4-Chlorophenyl | (trans-4-Hydroxycyclohexyl)amino | 173 |
| 134 | CF₃ | 4-Chlorophenyl | Cyclopentylamino | 99 |
| 135 | Phenyl | 4-Chlorophenyl | (trans-4-Hydroxycyclohexyl)amino | 95 |
| 136 | Isopropyl | 4-Chlorophenyl | 4-Hydroxypiperidino | 121 |
| 137 | Isopropyl | 4-Chlorophenyl | (4-Hydroxybutyl)amino | Oil |
| 138 | Isopropyl | 4-Chlorophenyl | (Benzimidazol-2-ylmethyl)amino | 112 |
| 139 | Isopropyl | 4-Chlorophenyl | Cyclobutylamino | 70 |
| 140 | Isopropyl | 4-Chlorophenyl | Cyclononylamino | Oil |
| 141 | Isopropyl | 4-Chlorophenyl | 3-Diethylaminocarbonyl-piperidino | Oil |
| 142 | Isopropyl | 4-Chlorophenyl | ((R)-1-Phenylethyl)-amino | Oil |
| 143 | Isopropyl | 4-Chlorophenyl | ((S)-1-Phenylethyl)-amino | Oil |

Example 144

2-(4-Chlorophenyl)-6-isopropyl-4-(1-oxothiomorpholino) pyrimidine 0.25 g of 2-(4-chlorophenyl)-6-isopropyl-4-thiomorpholinopyrimidine was dissolved in 1 ml of glacial acetic acid and treated with 0.068 ml of a 35% strength hydrogen peroxide solution. After 2 hours, the mixture was diluted with 20 ml of water and the product was extracted with ethyl acetate. The ethyl acetate phase was extracted twice by shaking with 10 ml of water and the organic phase was concentrated after drying over sodium sulfate. The residue was recrystallized from isopropanol. Yield: 0.18 g. M.p.: 171° C.

The following sulfoxides and sulfones were prepared analogously:

Example 145

2-(4-Chlorophenyl)-6-isopropyl-4-(1,1-dioxothiomorpholino)pyrimidine; m.p.: 226° C.

Example 146

2-(4-Chlorophenyl)6-isopropyl-4-(1-oxo-1,3-thiazolidin-1-yl)pyrimidine; m.p.: 128° C.

Example 147

2-(4-Chlorophenyl)-4-((2-ethylsulfinylethyl)amino)-6-isopropylpyrimidine; m.p.: 103° C.

Example 148

6-Isopropyl-2-(4-methylphenyl)-4-(1-oxothiomorpholino)pyrimidine; m.p.: 152° C.

Example 149

2-(3,5-dichlorophenyl)-6-isopropyl-4-(1-oxothiomorpholino)pyrimidine; m.p.: 187° C.

Pharmacological Investigations

Activation of Soluble Guanylate Cyclase

The activation of soluble guanylate cyclase (sGC), which catalyzes the conversion of guanosine triphosphate (GTP) to cyclic guanosine monophosphate (cGMP) and pyrophosphate, by the compounds according to the invention was quantified with the aid of an enzyme immunoassay (EIA) from Amersham. For this, the test substances were first incubated with sGC in microtiter plates and then the quantity of the resulting cGMP was determined.

The sGC employed had been isolated from bovine lung (see Methods in Enzymology, Volume 195, p. 377). The test solutions (100 μl per well) contained 50 mM triethanolamine (TEA) buffer (pH 7.5), 3 mM $MgCl_2$, 3 mM reduced glutathione (GSH), 0.1 mM GTP, 1 mM 3-isobutyl-1-methylxanthine (IBMX), suitably diluted enzyme solution and the test substance or, in the control experiments, solvent. The test substances were dissolved in dimethyl sulfoxide (DMSO) and the solution was diluted with DMSO/water such that the final concentration c of test substance in the test batch was 50 μM. The DMSO concentration in the test batch was 5% (v/v). The reaction was started by addition of the sGC. The reaction mix was incubated at 37° C. for 15 to 20 minutes and then stopped by ice-cooling and addition of the stop reagent (50 mM EDTA, pH 8.0). An aliquot of 50 μl was taken and employed for the determination of the cGMP content using the acetylation protocol of the Amersham cGMP EIA kit. The absorption of the samples was measured at 450 nm (reference wavelength 620 nm) in a microtiter plate reading apparatus. The cGMP concentration was determined by means of a calibration curve, which was obtained under the same experimental conditions. The activation of the sGC by a test substance is indicated as n-fold stimulation of the basal enzyme activity which was found in the control experiments (with solvent instead of test substance) (calculated according to the formula n-fold stimulation=$[cGMP]_{test\ substance}/[cGMP]_{control}$.

The following results were obtained:

| Compound of Example No. | n-fold stimulation at c = 50 μM |
|---|---|
| 23 | >8 |
| 25 | 28 |
| 29 | >4 |
| 30 | >4 |
| 32 | >4 |
| 33 | >16 |
| 34 | >4 |
| 35 | >16 |
| 36 | >8 |
| 38 | >8 |
| 43 | >4 |
| 44 | >4 |
| 45 | >4 |
| 52 | >8 |
| 63 | >4 |
| 66 | >4 |
| 69 | >4 |
| 77 | 30 |
| 79 | >4 |
| 80 | >16 |
| 81 | >4 |
| 82 | >4 |
| 84 | >16 |
| 85 | >16 |
| 86 | >16 |
| 88 | >8 |
| 89 | >8 |
| 90 | >16 |
| 97 | >16 |
| 98 | >8 |
| 99 | >4 |

-continued

| Compound of Example No. | n-fold stimulation at c = 50 μM |
|---|---|
| 100 | >8 |
| 112 | >8 |
| 124 | >16 |
| 125 | 32 |
| 133 | >16 |
| 137 | >16 |

What is claimed is:
1. A compound of the formula I,

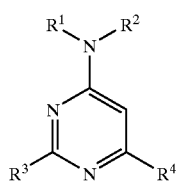

I in which
- $R^1$ is $(C_1-C_8)$-alkyl, which can be substituted by one or more identical or different substituents chosen from hydroxyl, $(C_1-C_4)$-alkoxy, $(C_1-C_4)$-alkyl-$S(O)_m$—, $R^5R^6N$ and aryl; $(C_3-C_9)$-cycloalkyl, which can be substituted by one or more identical or different substituents chosen from $(C_1-C_4)$-alkyl, hydroxyl and amino; or a radical of a 5-membered to 7-membered saturated heterocyclic ring with one or two identical or different hetero ring members chosen from O, $NR^7$ and $S(O)_m$ and that can be substituted by one or more identical or different substituents chosen from $(C_1-C_4)$-alkyl and aryl-$(C_1-C_4)$-alkyl-; and
- $R^2$ is hydrogen, $(C_1-C_8)$-alkyl, which can be substituted by one or more identical or different substituents chosen from hydroxyl, $(C_1-C_4)$-alkoxy, $(C_1-C_4)$-alkyl-$S(O)_m$—, $R^5R^6N$ and aryl; $(C_3-C_9)$-cycloalkyl, which can be substituted by one or more identical or different substituents chosen from $(C_1-C_4)$-alkyl, hydroxyl and amino; or the radical of a 5-membered to 7-membered saturated heterocyclic ring with one or two identical or different hetero ring members chosen from O, $NR^7$ and $S(O)_m$ and that can be substituted by one or more identical or different substituents chosen from $(C_1-C_4)$-alkyl and aryl-$(C_1-C_4)$-alkyl-; or
- $R^1R^2N$ is a radical, bonded via a ring nitrogen atom, of a 5-membered to 7-membered saturated heterocyclic ring optionally with, in addition to the nitrogen atom carrying the radicals $R^1$ and $R^2$, a further hetero ring member chosen from O, $NR^7$ and $S(O)_m$ and that can be substituted by one or more identical or different substituents chosen from $(C_1-C_4)$-alkyl, hydroxyl, $(C_1-C_4)$-alkoxy, $R^8R^9N$, hydroxycarbonyl, $(C_1-C_4)$-alkoxycarbonyl and $R^8R^9N$—CO—;
- $R^3$ is phenyl, which can be substituted by one or more identical or different substituents chosen from halogen, $(C_1-C_4)$-alkyl, phenyl, $CF_3$, $NO_2$, OH, —O—$(C_1-C_4)$-alkyl, —O$(C_2-C_4)$-alkyl-O—$(C_1-C_4)$-alkyl, $(C_1-C_2)$-alkylenedioxy, $NH_2$, —NH—$(C_1-C_4)$-alkyl, $N((C_1-C_4)$-alkyl$)_2$, —NH—CHO, —NH—CO—$(C_1-C_4)$-alkyl, —CN, —CO—$NH_2$, —CO—NH—$(C_1-C_4)$-alkyl, —CO—N$((C_1-C_4)$-alkyl$)_2$, —CO—OH, —CO—O—$(C_1-C_4)$-alkyl, —CHO and —CO—$(C_1-C_4)$-alkyl;
- $R^4$ is $(C_2-C_5)$-alkyl, trifluoromethyl or phenyl, which can be substituted by one or more identical or different substituents chosen from halogen, $(C_1-C_4)$-alkyl, phenyl, $CF_3$, $NO_2$, OH, —O—$(C_1-C_4)$-alkyl, —O—$(C_2-C_4)$-alkyl-O—$(C_1-C_4)$-alkyl, $(C_1-C_2)$-alkylenedioxy, $NH_2$, —NH—$(C_1-C_4)$-alkyl, $N((C_1-C_4)$-alkyl$)_2$, —NH—CHO, —NH—CO—$(C_1-C_4)$-alkyl, —CN, —CO—$NH_2$, —CO—NH—$(C_1-C_4)$-alkyl, —CO—N$((C_1-C_4)$-alkyl$)_2$, —CO—OH, —CO—O—$(C_1-C_4)$-alkyl, —CHO and —CO—$(C_1-C_4)$-alkyl;
- $R^5$ and $R^6$ are identical or different radicals chosen from hydrogen and $(C_1-C_4)$-alkyl; or the group $R^5R^6N$ is a radical, bonded via a ring nitrogen atom, of a 5-membered to 7-membered saturated or unsaturated heterocyclic ring optionally with, in addition to the nitrogen atom carrying the radicals $R^5$ and $R^6$, a further hetero ring member chosen from an oxygen atom, a group $S(O)_m$ and a nitrogen atom and that can carry on ring carbon atoms one or more identical or different substituents chosen from $(C_1-C_4)$-alkyl, hydroxyl and amino and that can carry on a ring nitrogen atom a radical $R^7$;
- $R^7$ is hydrogen, $(C_1-C_4)$-alkyl, aryl-$(C_1-C_4)$-alkyl-, hydroxy-$(C_1-C_4)$-alkyl, hydroxycarbonyl-$(C_1-C_4)$-alkyl-, $((C_1-C_4)$-alkoxycarbonyl$)$-$(C_1-C_4)$-alkyl, $R^8R^9N$—CO—$(C_1-C_4)$-alkyl-, $R^{10}$—$SO_2$— or aryl; where $R^7$, if this group is present on a piperazino radical representing $R^1R^2N$, cannot be carbocyclic aryl or carbocyclic aryl-$(C^1-C^4)$-alkyl;
- $R^8$ and $R^9$ are identical or different radicals chosen from hydrogen and $(C_1-C_4)$-alkyl;
- $R^{10}$ is $(C_1-C_4)$-alkyl, aryl or $R^8R^9N$;
- aryl is phenyl, naphthyl or heteroaryl, all of which can be substituted by one or more identical or different substituents chosen from halogen, $(C_1-C_4)$-alkyl, phenyl, $CF_3$, $NO_2$, OH, —O—$(C_1-C_4)$-alkyl, O—$(C_2-C_4)$-alkyl-O—$(C_1-C_4)$-alkyl, $(C_1-C_2)$-alkylenedioxy, $NH_2$, —NH—$(C_1-C_4)$-alkyl, —N$((C_1-C_4)$-alkyl$)_2$, —NH—CHO, —NH—CO—$(C_1-C_4)$-alkyl, —CN, CO—$NH_2$, —CO—NH—$(C_1-C_4)$alkyl, —CO—N$((C_1-C_4)$-alkyl$)_2$, —CO—OH, —CO—O—$(C_1-C_4)$-alkyl, —CHO and —CO—$(C_1-C_4)$-alkyl;
- heteroaryl is the radical of a monocyclic 5-membered or 6-membered aromatic heterocycle or of a bicyclic 8-membered to 10-membered aromatic heterocycle, each of which with one or two identical or different ring heteroatoms chosen from N, O and S;
- m is 0, 1 or 2;
- or a stereoisomeric form of a compound of formula I,
- or a mixture of stereoisomeric forms of compounds of formula I in all ratios,
- or a physiologically tolerable salt of a compound of formula I,
- or a physiologically tolerable salt of a stereoisomeric form of a compound of formula I;
- compounds of the formula I being excluded in which, simultaneously, $R^4$ is ethyl, tert-butyl, trifluoromethyl, or unsubstituted phenyl; $R^3$ is phenyl, which can be substituted by one or two identical or different substituents chosen from halogen, OH, —O—$R^{11}$ and $CF_3$, $R^1R^2N$ is $R^{11}$—NH—, $(R^{11})_2N$— or $R^{12}R^{13}N$—$(CH_2)_p$—NH—; p is 2 or 3; $R^{11}$ is saturated unsubstituted $(C_1-C_4)$-alkyl; and $R^{12}$ and $R^{13}$ are identical or different radicals chosen from hydrogen and $R^{11}$ or the group $R^{12}R^{13}N$ is a radical, bonded via a ring nitrogen atom, of a 5-membered or 6-membered saturated heterocyclic ring optionally with, in addition to the nitrogen atom carrying the radicals $R^{12}$ and $R^{13}$, a further hetero ring member chosen from an oxygen atom, a sulfur atom and a nitrogen atom and that can be substituted by an aryl radical or by an aryl-$(C_1-C_4)$-alkyl radical, wherein the aryl group can be substituted by one or two identical or different substituents chosen from halogen, OH, —O—$R^{11}$, and $CF_3$.

2. A compound of claim 1, in which
$R^1$ is $(C_1-C_8)$-alkyl, which can be substituted by one or more identical or different substituents, chosen from, hydroxyl, $(C_1-C_4)$-alkoxy, $(C_1-C_4)$-alkyl-$S(O)_m$—, $R^5R^6N$ and aryl; or is $(C_3-C_9)$-cycloalkyl, which can be substituted by one or more identical or different substituents chosen from $(C_1-C_4)$-alkyl, hydroxyl and amino; and $R^2$ is hydrogen, $(C_1-C_8)$-alkyl, which can be substituted by one or more identical or different substituents chosen from hydroxyl, $(C_1-C_4)$-alkoxy, $(C_1-C_4)$ alkyl-$S(O)_m$—, $R^5R^6N$ and aryl; or is $(C_3-C_9)$-cycloalkyl, which can be substituted by one or more identical or different substituents chosen from $(C_1-C_4)$-alkyl, hydroxyl and amino; or $R^1R^2N$ is a radical, bonded via a ring nitrogen atom of a 5-membered, 6-membered or 7-membered saturated heterocyclic ring optionally with, in addition to the nitrogen atom carrying the radicals $R^1$ and $R^2$, a further hetero ring member chosen from an oxygen atom, a group $S(O)_m$ and a nitrogen atom carrying a radical $R^7$ and that can be substituted by one or more identical or different substituents chosen from $(C_1-C_4)$-alkyl, hydroxyl, $(C_1-C_4)$-alkoxy, $R^8R^9N$, hydroxycarbonyl, $(C_1-C_4)$-alkoxycarbonyl and $R^8R^9N$—CO.

3. A compound of claim 1, in which $R^1$ is $(C_1-C_4)$alkyl, which can be substituted by one or more identical or different substituents chosen from hydroxyl, $(C_1-C_4)$-alkoxy, $(C_1-C_4)$-alkyl-$S(O)_m$—, $R^5R^6N$ and aryl, or $(C_3-C_9)$ cycloalkyl, which can be substituted by one or more identical or different substituents chosen from $(C_1-C_4)$-alkyl, hydroxyl and amino, and $R^2$ is hydrogen; or $R^1$ and $R^2$ are identical or different $(C_1-C_4)$-alkyl, which can be substituted by one or more identical or different substituents chosen from hydroxyl, $(C_1-C_4)$-alkoxy, $(C_1-C_4)$-alkyl-$S(O)_m$—, $R^5R^6N$ and aryl.

4. A compound of claim 1, in which $R^1$ is $(C_3-C_9)$-cycloalkyl, which can be substituted by one or more identical or different substituents chosen from $(C_1-C_4)$-alkyl, hydroxyl and amino, and $R^2$ is hydrogen.

5. A compound of claim 1, in which $R^1R^2N$— is an unsubstituted or substituted radical chosen from piperidino, morpholino and thiomorpholino (and its S-oxide and S,S-dioxide) and piperazino.

6. A compound of the formula I,

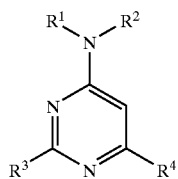

in which
$R^1$ is $(C_1-C_8)$-alkyl, which can be substituted by one or more identical or different substituents chosen from hydroxyl, $(C_1-C_4)$-alkoxy, $(C_1-C_4)$-alkyl—$S(O)_m$—, $R^5R^6N$ and aryl; $(C_3-C_9)$-cycloalkyl, which can be substituted by one or more identical or different substituents chosen from $(C_1-C_4)$-alkyl, hydroxyl and amino; or a radical of a 5-membered to 7-membered saturated heterocyclic ring with one or two identical or different hetero ring members chosen from O, $NR^7$ and $S(O)_m$ and that can be substituted by one or more identical or different substituents chosen from $(C_1-C_4)$-alkyl and aryl-$(C_1-C_4)$-alkyl-; and $R^2$ is hydrogen, $(C_1-C_8)$-alkyl, which can be substituted by one or more identical or different substituents chosen from hydroxyl, $(C_1-C_4)$-alkoxy, $(C_1-C_4)$ -alkyl-$S(O)_m$—, $R^5R^6N$ and aryl; $(C_3-C_9)$-cycloalkyl, which can be substituted by one or more identical or different substituents chosen from $(C_1-C_4)$-alkyl, hydroxyl and amino; or the radical of a 5-membered to 7-membered saturated heterocyclic ring with one or two identical or different hetero ring members chosen from O, $NR^7$ and $S(O)_m$ and that can be substituted by one or more identical or different substituents chosen from $(C_1-C_4)$-alkyl and aryl-$(C_1-C_4)$-alkyl-; or $R^1R^2N$ is a radical, bonded via a ring nitrogen atom, of a 5-membered to 7-membered saturated heterocyclic ring optionally with, in addition to the nitrogen atom carrying the radicals $R^1$ and $R^2$, a further hetero ring member chosen from O, $NR^7$ and $S(O)_m$ and that can be substituted by one or more identical or different substituents chosen from $(C_1-C_4)$-alkyl, hydroxyl, $(C_1-C_4)$-alkoxy, $R^8R^9N$, hydroxycarbonyl, $(C_1-C_4)$-alkoxycarbonyl and $R^8R^9N$—CO—;

$R^3$ is phenyl, which is substituted by one or more identical or different substituents chosen from halogen, $(C_1-C_4)$-alkyl, phenyl, $CF_3$, $NO_2$, OH, —O—$(C_1-C_4)$-alkyl, —O—$(C_2-C_4)$-alkyl, —O—$(C_1-C_4)$-alkyl, $(C_1-C_2)$-alkylenedioxy, $NH_2$—NH—$(C_1-C_4)$-alkyl, $N((C_1-C_4)$-alkyl$)_2$, —NH—CHO, —NH—CO—$(C_1-C_4)$-alkyl, —CN, —CO—$NH_2$, —CO—NH—$(C_1-C_4)$-alkyl, —CO—N$((C_1-C_4)$-alkyl$)_2$, —CO—OH, —CO—O—$(C_2-C_4)$-alkyl, —CHO and —CO—$(C_1-C_4)$-alkyl;

$R^4$ is $(C_1-C_5)$-alkyl, trifluoromethyl or phenyl, which can be substituted by one or more identical or different substituents chosen from halogen, $(C_1-C_4)$-alkyl, phenyl, $CF_3$, $NO_2$, OH, —O—$(C_1-C_4)$-alkyl, —O—$(C_2-C_4)$-alkyl-O—$(C_1-C_4)$-alkyl, $(C_1-C_2)$-alkylenedioxy $NH_2$, —NH—$(C_1-C_4)$-alkyl, $N((C_1-C_4)$-alkyl$)_2$, —NH—CHO, —NH—CO—$(C_1-C_4)$-alkyl, —CN, —CO—$NH_2$, —CO—NH—$(C_1-C_4)$-alkyl, —CO—N$((C_1-C_4)$-alkyl$)_2$, —CO—OH, —CO—O—$(C_1-C_4)$-alkyl, —CHO and —CO—$(C_1-C_4)$-alkyl;

$R^5$ and $R^6$ are identical or different radicals chosen from hydrogen and $(C_1-C_4)$-alkyl; or the group $R^5R^6N$ is a radical, bonded via a ring nitrogen atom, of a 5-membered to 7-membered saturated or unsaturated heterocyclic ring optionally with, in addition to the nitrogen atom carrying the radicals $R^5$ and $R^6$, a further hetero ring member chosen from an oxygen atom, a group $S(O)_m$ and a nitrogen atom and that can carry on ring carbon atoms one or more identical or different substituents chosen from $(C_1-C_4)$-alkyl, hydroxyl and amino and that can carry on a ring nitrogen atom a radical $R^7$;

$R^7$ is hydrogen, $(C_1-C_4)$-alkyl, aryl-$(C_1-C_4)$-alkyl-, hydroxy-$(C_1-C_4)$alkyl, hydroxycarbonyl-$(C_1-C_4)$- alkyl-, ((C$_1$–C$_4$)alkoxycarbonyl)-(C$_1$–C$_4$)-alkyl, R$^8$R$^9$N—CO—(C$_1$–C$_4$)-alkyl-, R$^{10}$—SO$_2$— or aryl; where R$^7$, if this group is present on a piperazino radical representing R$^1$R$^2$N, cannot be carbocyclic aryl or carbocyclic aryl-(C$^1$–C$^4$)-alkyl;

R$^8$ and R$^9$ are identical or different radicals chosen from hydrogen and (C$_1$–C$_4$)-alkyl;

R$^{10}$ is (C$_1$–C$_4$)-alkyl, aryl or R$^8$R$^9$N;

aryl is phenyl, naphthyl or heteroaryl, all of which can be substituted by one or more identical or different substituents chosen from halogen, (C$_1$–C$_4$)alkyl, phenyl, CF$_3$, NO$_2$, OH, —O—(C$_1$–C$_4$)-alkyl, O—(C$_2$–C$_4$)-alkyl-O—(C$_1$–C$_4$)-alkyl, (C$_1$–C$_2$)-alkylenedioxy, NH$_2$, —NH—(C$_1$–C$_4$)-alkyl, —N((C$_1$–C$_4$)-alkyl)$_2$—NH—CHO, —NH—CO—(C$_1$–C$_4$)-alkyl, —CN, CO—NH$_2$, —CO—NH—(C$_1$–C$_4$)-alkyl, —CO—N((C$_1$–C$_4$)-alkyl)$_2$, —CO—OH, —CO—O—(C$_1$–C$_4$)-alkyl, —CHO and —CO—(C$_1$–C$_4$)-alkyl;

heteroaryl is the radical of a monocyclic 5-membered or 6-membered aromatic heterocycle or of a bicyclic 8-membered to 10-membered aromatic heterocycle, each of which with one or two identical or different ring heteroatoms chosen from N, O and S;

m is 0, 1 or 2;

or a stereoisomeric form of a compound of formula I, or a mixture of stereoisomeric forms of compounds of formula I in all ratios, or a physiologically tolerable salt of a compound of formula I, or a physiologically tolerable salt of a stereoisomeric form of a compound of formula I;

compounds of the formula I being excluded in which, simultaneously, R$^4$ is ethyl, tert-butyl, or trifluoromethyl; R$^3$ is phenyl, which is substituted by one or two identical or different substituents chosen from halogen, OH, —O—R$^{11}$ and CF$_3$, R$^1$R$^2$N is R$^{11}$—NH—, (R$^{11}$)$_2$N— or R$^{12}$R$^{13}$N—(CH$_2$)$_p$—NH—; p is 2 or 3; R$^{11}$ is saturated unsubstituted (C$_1$–C$_4$)-alkyl; and R$^{12}$ and R$^{13}$ are identical or different radicals chosen from hydrogen and R$^{11}$ or the group R$^{12}$R$^{13}$N is a radical, bonded via a ring nitrogen atom, of a 5-membered or 6-membered saturated heterocyclic ring optionally with, in addition to the nitrogen atom carrying the radicals R$^{12}$ and R$^{13}$, a further hetero ring member chosen from an oxygen atom, a sulfur atom and a nitrogen atom and that can be substituted by an aryl radical or by an aryl-(C$_1$–C$_4$)-alkyl radical, wherein the aryl group can be substituted by one or two identical or different substituents chosen from halogen, OH, —O—R$^{11}$, and CF$_3$.

7. A compound of claim 1, in which R$^4$ is (C$_3$–C$_4$)-alkyl.

8. A compound of claim 5, in which R$^3$ is substituted phenyl.

9. A compound of claim 5, in which R$^4$ is (C$_3$–C$_4$)-alkyl.

10. A compound of claim 1, in which R$^1$ is (C$_3$–C$_7$)-cycloalkyl, which can be substituted by one or two identical or different substituents chosen from (C$_1$–C$_4$)-alkyl, hydroxyl and amino, and R$^2$ is hydrogen.

11. A compound of claim 1, in which R$^1$ is (C$_3$–C$_9$)-cloalkyl, which is substituted by hydroxyl and R$^2$ is hydrogen.

12. A compound of claim 1, in which R$^1$ is cyclopentyl or cyclohexyl, wherein said cyclopentyl or cyclohexyl can be substituted by one or more identical or different substituents chosen from (C$_1$–C$_4$)-alkyl, hydroxyl and amino, and R$^2$ is hydrogen.

13. A compound of claim 1, in which R$^1$ is cyclopentyl or cyclohexyl, wherein said cyclopentyl or cyclohexyl is substituted by one or two identical or different substituents chosen from (C$_1$–C$_4$)-alkyl, hydroxyl and amino, and R$^2$ is hydrogen.

14. A compound of claim 1, in which R$^1$ is cyclopentyl or cyclohexyl, wherein said cyclopentyl or cyclohexyl is substituted by hydroxyl, and R$^2$ is hydrogen.

15. A compound of claim 1, in which R$^1$ is cyclohexyl, which is substituted by hydroxyl, and R$^2$ is hydrogen.

16. A compound of claim 1, in which R$^1$ is 4-hydroxycyclohexyl and R$^2$ is hydrogen.

17. A compound of claim 1, in which R$^1$ is (C$_1$–C$_8$)-alkyl, which can be substituted by one or more identical or different substituents chosen from hydroxyl, (C$_1$–C$_4$)-alkoxy, (C$_1$–C$_4$)-alkyl-S(O)$_m$—, R$^5$R$^6$N— and aryl, and R$^2$ is hydrogen.

18. A compound of the formula I, $$\underset{R^3 \quad N}{\underset{\|}{\overset{R^1\diagdown N \diagup R^2}{\underset{|}{\bigg\langle}}}\overset{N}{\phantom{X}}R^4} \qquad \text{I}$$

in which

R$^1$R$^2$N is cyclopentylamino, R$^3$ is 4-methylphenyl, and R$^4$ is isopropyl; or R$^1$R$^2$N is (trans-4-hydroxycyclohexyl)amino, R$^3$ is 4-methylphenyl, and R$^4$ is isopropyl; or R$^1$R$^2$N is cyclopropylamino, R$^3$ is 4-chlorophenyl, and R$^4$ is isopropyl; or R$^1$R$^2$N is (trans-4-hydroxycyclohexyl)amino, R$^3$ is 3,5-dichlorophenyl, and R$^4$ is isopropyl; or R$^1$R$^2$N is cyclopentylamino, R$^3$ is 4-cyanophenyl, and R$^4$ is isopropyl; or R$^1$R$^2$N is (4-hydroxycyclohexyl)amino, R$^3$ is 4-cyanophenyl, and R$^4$ is isopropyl; or R$^1$R$^2$N is cyclopentylamino, R$^3$ is 4-chlorophenyl, and R$^4$ is isopropyl; or R$^1$R$^2$N is (trans-4-hydroxycyclohexyl)amino, R$^3$ is 4-chlorophenyl, and R$^4$ is isopropyl; or R$^1$R$^2$N is (trans-4-aminocyclohexyl)amino, R$^3$ is 4-chlorophenyl, and R$^4$ is isopropyl; or R$^1$R$^2$N is (cis/trans-4-hydroxycyclohexyl)amino, R$^3$ is 4-chlorophenyl, and R$^4$ is isopropyl; or R$^1$R$^2$N is (4-methylcyclohexyl)amino, R$^3$ is 4-chlorophenyl, and R$^4$ is isopropyl; or R$^1$R$^2$N is (2-isopropyl-5-methylcyclohexyl)amino, R$^3$ is 4-chlorophenyl, and R$^4$ is isopropyl; or R$^1$R$^2$N is (trans-2-hydroxycyclohexyl)amino, R$^3$ is 4-chlorophenyl, and R$^4$ is isopropyl; or R$^1$R$^2$N is cyclopentylamino, R$^3$ is 4-chlorophenyl, and R$^4$ is tert-butyl; or R$^1$R$^2$N is (trans-4-hydroxycyclohexyl)amino, R$^3$ is 4-chlorophenyl, and R$^4$ is tert-butyl; or R$^1$R$^2$N is cyclopentylamino, R$^3$ is 4-chlorophenyl, and R$^4$ is CF$^3$, or R$^1$R$^2$N is (trans-4-hydroxycyclohexyl)amino, R$^3$ is 4-chlorophenyl, and R$^4$ is phenyl; or R$^1$R$^2$N is cyclobutylamino, R$^3$ is 4 chlorophenyl, and R$^4$ is isopropyl; or $R^1R^2N$ is cyclononylamino, $R^3$ is 4-chlorophenyl, and $R^4$ is isopropyl;

or a stereoisomeric form of a compound of formula I, or a mixture of stereoisomeric forms of compounds of formula I in all ratios, or a physiologically tolerable salt of a compound of formula I, or a physiologically tolerable salt of a stereoisomeric form of a compound of formula I.

19. A compound of claim 18, wherein in the formula I $R^1R^2N$ is (trans-4-hydroxycyclohexyl)amino, $R^3$ is 4-methylphenyl, and $R^4$ is isopropyl; or $R^1R^2N$ is (trans-4-hydroxycyclohexyl)amino, $R^3$ is 3,5-dichlorophenyl, and $R^4$ is isopropyl; or $R^1R^2N$ is (4-hydroxycyclohexyl)amino, $R^3$ is 4-cyanophenyl, and $R^4$ is isopropyl; or $R^1R^2N$ is (trans-4-hydroxycyclohexyl)amino, $R^3$ is 4-chlorophenyl, and $R^4$ is isopropyl; or $R^1R^2N$ is (cis/trans-4-hydroxycyclohexyl)amino, $R^3$ is 4-chlorophenyl, and $R^4$ is isopropyl; or $R^1R^2N$ is (trans-2-hydroxycyclohexyl)amino, $R^3$ is 4-chlorophenyl, and $R^4$ is isopropyl; or $R^1R^2N$ is (trans-4-hydroxycyclohexyl)amino, $R^3$ is 4-chlorophenyl, and $R^4$ is tert-butyl; or $R^1R^2N$ is (trans-4-hydroxycyclohexyl)amino, $R^3$ is 4-chlorophenyl, and $R^4$ is phenyl.

20. A compound of the formula I,

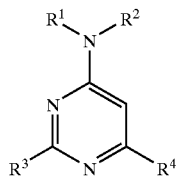

in which $R^1$ is $(C_3-C_7)$-cloalkyl, which can be substituted by one or two identical or different substituents chosen from $(C_1-C_4)$-alkyl, hydroxyl and amino;

$R^2$ is hydrogen;

$R^3$ is phenyl, which can be substituted by one or more identical or different substituents chosen from halogen, $(C_1-C_4)$-alkyl, phenyl, $CF_3$, $NO_2$, OH, —O—$(C_1-C_4)$alkyl, —O—$(C_2-C_4)$-alkyl-O—$(C_1-C_4)$-alkyl, $(C_1-C_2)$-alkylenedioxy, $NH_2$, —NH—$(C_1-C_4)$-alkyl, $N((C_1-C_4)$-alkyl$)_2$, —NH—CHO, —NH—CO—$(C_1-C_4)$-alkyl, —CN, —CO—$NH_2$, —CO—NH—$(C_1-C_4)$-alkyl, —CO—N$((C_1-C_4)$-alkyl$)_2$, —CO—OH, —CO—O—$(C_1-C_4)$-alkyl, —CHO and —CO—$(C_1-C_4)$alkyl; and $R^4$ is $(C_2-C_5)$alkyl, trifluoromethyl or phenyl, which can be substituted by one or more identical or different substituents chosen from halogen, $(C_1-C_4)$-alkyl, phenyl, $CF_3$, $NO_2$, OH, —O—$(C_1-C_4)$-alkyl, —O—$(C_1-C_4)$-alkyl-O—$(C_1-C_4)$-alkyl, $(C_1-C_2)$-alkylenedioxy, $NH_2$, —NH—$(C_1-C_4)$-alkyl, $N((C_2-C_4)$-alkyl$)_2$, —NH—CHO, —NH—CO—$(C_1-C_4)$-alkyl, —CN, —CO—$NH_2$, —CO—$NH_2$, —CO—NH—$(C_1-C_4)$-alkyl, —CO—N$((C_1-C_4)$-alkyl$)_2$, —CO—OH, —CO—O—$(C_1-C_4)$-alkyl, —CHO and —CO—$(C_1-C_4)$-alkyl;

or a stereoisomeric form of a compound of formula I, or a mixture of stereoisomeric forms of compounds of formula I in all ratios, or a physiologically tolerable salt of a compound of formula I, or a physiologically tolerable salt of a stereoisomeric form of a compound of formula I.

21. A process for the preparation of at least one compound of claim 1, which comprises activating a 4-hydroxypyrimidine of the formula IV and then reacting it with an amine of a formula VI to produce a compound of formula I,

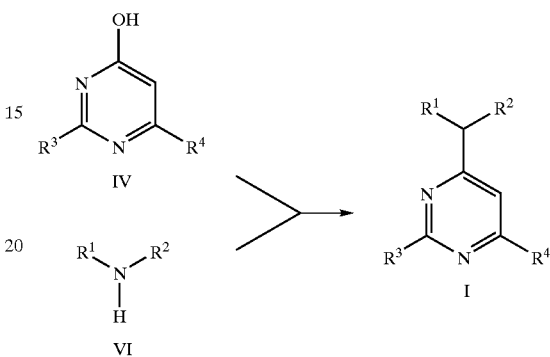

and optionally converting a compound of formula I into a pharmaceutically acceptable salt.

22. A process for the preparation of at least one compound of claim 5, which comprises-activating a 4-hydroxypyrimidine of the formula IV and then reacting it with an amine of a formula VI;

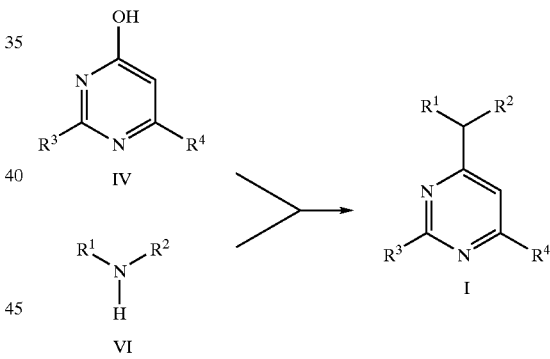

and optionally converting the resulting product into a pharmaceutically acceptable salt.

23. A pharmaceutical composition, comprising one or more compounds of claim 1 and a pharmaceutically acceptable carrier.

24. A pharmaceutical composition, comprising one or more compounds of claim 5 and a pharmaceutically acceptable carrier.

25. A method of treating angina pectoris, comprising administering to a patient in need thereof an effective amount of at least one compound of claim 1.

26. A method of treating angina pectoris, comprising administering to a patient in need thereof an effective amount of at least one compound of claim 5.

27. A method of treating angina pectoris, comprising administering to a patient in need thereof an effective amount of at least one compound of formula I,

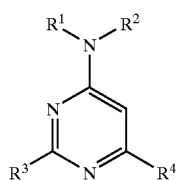

in which
- $R^1$ is $(C_1-C_8)$-alkyl, which can be substituted by one or more identical or different substituents chosen from hydroxyl, $(C_1-C_4)$-alkoxy, $(C_1-C_4)$-alkyl—$S(O)_m$—, $R^5R^6N$ and aryl; $(C_3-C_9)$-cycloalkyl, which can be substituted by one or more identical or different substituents chosen from $(C_1-C_4)$-alkyl, hydroxyl and amino; or a radical of a 5-membered to 7-membered saturated heterocyclic ring with one or two identical or different hetero ring members chosen from O, $NR^7$ and $S(O)_m$ and that can be substituted by one or more identical or different substituents chosen from $(C_1-C_4)$-alkyl and aryl-$(C_1-C_4)$-alkyl; and
- $R^2$ is hydrogen, $(C_1-C_8)$-alkyl, which can be substituted by one or more identical or different substituents chosen from hydroxyl, $(C_1-C_4)$-alkoxy, $(C_1-C_4)$-alkyl—$S(O)_m$—, $R^5R^6N$ and aryl; $(C_3-C_9)$-cloalkyl, which can be substituted by one or more identical or different substituents chosen from $(C_1-C_4)$-alkyl, hydroxyl and amino; or the radical of a 5-membered to 7-membered saturated heterocyclic ring with one or two identical or different hetero ring members chosen from O, $NR^7$ and $S(O)_m$ and, that can be substituted by one or more identical or different substituents chosen from $(C_1-C_4)$-alkyl and aryl-$(C_1-C_4)$-alkyl-; or
- $R^1R^2N$ is a radical, bonded via a ring nitrogen atom, of a 5-membered to 7-membered saturated heterocyclic ring optionally with, in addition to the nitrogen atom carrying the radicals $R^1$ and $R^2$, a further hetero ring member chosen from O, $NR^7$ and $S(O)_m$ and that can be substituted by one or more identical or different substituents chosen from $(C_1-C_4)$-alkyl, hydroxyl, $(C_1-C_4)$-alkoxy, $R^8R^9N$, hydroxycarbonyl, $(C_1-C_4)$-alkoxycarbonyl and $R^8R^9N$—CO—;
- $R^3$ is phenyl, which can be substituted by one or more identical or different substituents chosen from halogen, $(C_1-C_4)$-alkyl, phenyl, $CF_3$, $NO_2$, OH, —O—$(C_1-C_4)$alkyl, —O—$(C_2-C_4)$-alkyl-O—$(C_1-C_4)$-alkyl, $(C_1-C_2)$-alkylenedioxy, $NH_2$, —NH—$(C_1-C_4)$-alkyl, $N((C_1-C_4)$-alkyl$)_2$, —NH—CHO, —NH—CO—$(C_1-C_4)$-alkyl, —CN, —CO—$NH_2$, —CO—NH—$(C_1-C_4)$-alkyl, —CO—N$((C_1-C_4)$-alkyl$)_2$, —CO—OH, —CO—O—$(C_1-C_4)$-alkyl, —CHO and —CO—$(C_1-C_4)$-alkyl;
- $R^4$ is $(C_2-C_5)$-alkyl, trifluoromethyl or phenyl, which can be substituted by one or more identical or different substituents chosen from halogen, $(C_1-C_4)$-alkyl, phenyl, $CF_3$, $NO_2$, OH, —O—$(C_1-C_4)$-alkyl, —O—$(C_2-C_4)$-alkyl—O—$(C_1-C_4)$alkyl, $(C_1-C_2)$-alkylenedioxy, $NH_2$, —NH—$(C_1-C_4)$-alkyl, $N((C_1-C_4)$alkyl$)_2$, —NH—CHO, —NH—CO—$(C_1-C_4)$-alkyl, —CN, —CO—$NH_2$, —CO—NH—$(C_1-C_4)$-alkyl, —CO—N$((C_1-C_4)$-alkyl$)_2$, —CO—OH, —CO—O—$(C_1-C_4)$-alkyl, —CHO and —CO—$(C_1-C_4)$-alkyl;
- $R^5$ and $R^6$ are identical or different radicals chosen from hydrogen and $(C_1-C_4)$-alkyl; or the group $R^5R^6N$ is a radical, bonded via a ring nitrogen atom, of a 5-membered to 7-membered saturated or unsaturated heterocyclic ring optionally with, in addition to the nitrogen atom carrying the radicals $R^5$ and $R^6$, a further hetero ring member chosen from an oxygen atom, a group $S(O)_m$ and a nitrogen atom and that can carry on ring carbon atoms one or more identical or different substituents chosen from $(C_1-C_4)$-alkyl, hydroxyl and amino and that can carry on a ring nitrogen atom a radical $R^7$;
- $R^7$ is hydrogen, $(C_1-C_4)$-alkyl, aryl-$(C_1-C_4)$-alkyl-, hydroxy-$(C_1-C_4)$-alkyl, hydroxycarbonyl-$(C_1-C_4)$-alkyl-, $((C_1-C_4)$-alkoxycarbonyl$)$-$(C_1-C_4)$-alkyl, $R^8R^9N$—CO—$(C_1-C_4)$-alkyl-, $R^{10}$—$SO_2$— or aryl; where $R^7$, if this group is present on a piperazino radical representing $R^1R^2N$, cannot be carbocyclic aryl or carbocyclic aryl $(C^1$—$C^4)$-alkyl;
- $R^8$ and $R^9$ are identical or different radicals chosen from hydrogen and $(C_1-C_4)$-alkyl;
- $R^{10}$ is $(C_1-C_4)$-alkyl, aryl or $R^8R^9N$;
- aryl is phenyl, naphthyl or heteroaryl, all of which can be substituted by one or more identical or different substituents chosen from halogen, $(C_1-C_4)$-alkyl, phenyl, $CF_3$, $NO_2$, OH, —O—$(C_1-C_4)$-alkyl, O—$(C_2-C_4)$-alkyl-O—$(C_1-C_4)$-alkyl, $(C_1-C_2)$-alkylenedioxy, $NH_2$, —NH—$(C_1-C_4)$-alkyl, —N$((C_1-C_4)$-alkyl$)_2$, —NH—CHO, —NH—CO—$(C_1-C_4)$-alkyl, —CN, CO—$NH_2$, —CO—NH—$(C_1-C_4)$-alkyl, —CO—N$((C_1-C_4)$-alkyl$)_2$, —CO—OH, —CO—O—$(C_1-C_4)$-alkyl, —CHO and —CO—$(C_1-C_4)$-alkyl;
- heteroaryl is the radical of a monocyclic 5-membered or 6-membered aromatic heterocycle or of a bicyclic 8-membered to 10-membered aromatic heterocycle, each of which with one or two identical or different ring heteroatoms chosen from N, O and S;
- m is 0, 1 or 2;
- or a stereoisomeric form of a compound of formula I,
- or a mixture of stereoisomeric forms of compounds of formula I in all ratios,
- or a physiologically tolerable salt of a compound of formula I,
- or a physiologically tolerable salt of a stereoisomeric form of a compound of formula I.

* * * * *

UNITED STATES PATENT AND TRADEMARK OFFICE
CERTIFICATE OF CORRECTION

PATENT NO. : 6,844,347 B1
APPLICATION NO. : 09/762893
DATED : January 18, 2005
INVENTOR(S) : Ursula Schindler et al.

It is certified that error appears in the above-identified patent and that said Letters Patent is hereby corrected as shown below:

Title Page,

Item (54), in the Title, lines 1-2, "4-AMINO-2ARYL-PYRIMIDINES" should read --4-AMINO-2-ARYL-PYRIMIDINES--.

Item (75), line 1, "Ursula Schnidler" should read --Ursula Schindler--.

Claims

Claim 16, column 14, line 32, "claim 15" should read --claim 12,--.

Claim 1, column 19, line 61, "-O($C_2$-$C_4$)-alkyl-O-($C_1$-$C_4$)-alkyl," should read -- -O-($C_2$-$C_4$)-alkyl-O-($C_1$-$C_4$)-alkyl,--.

Claim 1, column 19, lines 66-67, "-CO-($C_1$-$C_4$) -alkyl;" should read -- -CO-($C_1$-$C_4$)-alkyl;--.

Claim 1, column 20, line 42, "-CO-NH-($C_1$-$C_4$)alkyl," should read -- -CO-NH-($C_1$-$C_4$)-alkyl,--.

Claim 2, column 21, lines 20-21, "($C_1$-$C_4$) alkyl-S(O)$_m$-," should read --($C_1$-$C_4$)-alkyl-S(O)$_m$-,--.

Claim 3, column 21, lines 38-39, "($C_3$-$C_9$) cycloalkyl," should read --($C_3$-$C_9$)-cycloalkyl,--.

Claim 6, column 22, line 8, "S(O))$_m$" should read --S(O)$_m$--.

Claim 6, column 22, lines 13-14, "($C_1$-$C_4$) -alkyl-S(O)$_m$-," should read --($C_1$-$C_4$)-alkyl-S(O)$_m$-,--.

Claim 6, column 22, line 35, "-O-($C_2$-$C_4$)-alkyl, -O-($C_1$-$C_4$)-alkyl," should read -- -O-($C_2$-$C_4$)-alkyl-O-($C_1$-$C_4$)-alkyl,--.

Claim 6, column 22, line 36, "$NH_2$-NH-($C_1$-$C_4$)-alkyl," should read --$NH_2$, -NH-($C_1$-$C_4$)-alkyl,--.

Claim 6, column 22, line 40, "-CO-O-($C_2$-$C_4$)-alkyl," should read -- -CO-O-($C_1$-$C_4$)-alkyl,--.

Claim 6, column 22, line 42, "($C_1$-$C_5$)-alkyl," should read --($C_2$-$C_5$)-alkyl,--.

UNITED STATES PATENT AND TRADEMARK OFFICE
CERTIFICATE OF CORRECTION

PATENT NO.       : 6,844,347 B1
APPLICATION NO.  : 09/762893
DATED            : January 18, 2005
INVENTOR(S)      : Ursula Schindler et al.

It is certified that error appears in the above-identified patent and that said Letters Patent is hereby corrected as shown below:

Claim 6, column 22, lines 46-47, after "$(C_1-C_2)$-alkylenedioxy", insert a comma.

Claim 6, column 23, line 11, "$(C_1-C_4)$alkyl," should read --$(C_1-C_4)$-alkyl,--.

Claim 6, column 23, lines 14-15, "-$N((C_1-C_4)$-alkyl$)_2$-NH-CHO," should read -- -$N((C_1-C_4)$-alkyl$)_2$, -NH-CHO,--.

Claim 11, column 23, lines 60-61, "$(C_3-C_9)$-cloalkyl," should read --$(C_3-C_9)$-cycloalkyl,--.

Claim 18, column 24, line 66, "4 chlorophenyl," should read --4-chlorophenyl,--.

Claim 20, column 25, line 41, "$(C_3-C_7)$-cloalkyl," should read --$(C_3-C_7)$-cycloalkyl,--.

Claim 20, column 25, lines 47-48, "-O-$(C_1-C_4)$ alkyl," should read -- -O-$(C_1-C_4)$-alkyl,--.

Claim 20, column 25, lines 53-54, "-CO-$(C_1-C_4)$alkyl;" should read -- -CO-$(C_1-C_4)$-alkyl;--.

Claim 20, column 25, line 55, "$(C_2-C_5)$alkyl," should read --$(C_2-C_5)$-alkyl,--.

Claim 20, column 25, lines 58-59, "-O-$(C_1-C_4)$-alkyl-O-$(C_1-C_4)$-alkyl," should read -- -O-$(C_2-C_4)$-alkyl-O-$(C_1-C_4)$-alkyl,--.

Claim 20, column 25, line 61, "$N((C_2-C_4)$-alkyl$)_2$," should read --$N((C_1-C_4)$-alkyl$)_2$,--.

Claim 20, column 25, line 62, delete the second occurrence of "-CO-$NH_2$,".

Claim 21, column 26, in the structure for formula I between lines 14-22,

" 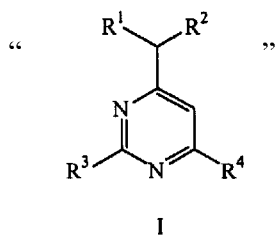 "

UNITED STATES PATENT AND TRADEMARK OFFICE
CERTIFICATE OF CORRECTION

PATENT NO. : 6,844,347 B1
APPLICATION NO. : 09/762893
DATED : January 18, 2005
INVENTOR(S) : Ursula Schindler et al.

It is certified that error appears in the above-identified patent and that said Letters Patent is hereby corrected as shown below:

should read

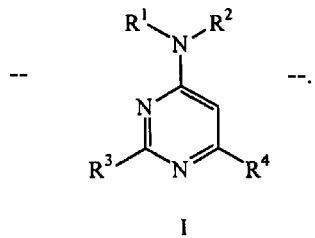

Claim 22, column 26, line 30, "comprises-activating" should read --comprises activating--.

Claim 22, column 26, in the structure for formula I between lines 37-45,

" 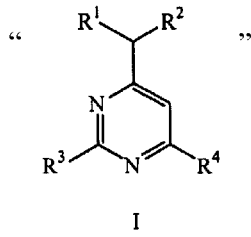 "

should read

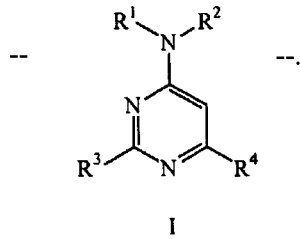

Claim 27, column 27, line 23, "aryl-$(C_1-C_4)$-alkyl;" should read --aryl-$(C_1-C_4)$-alkyl-;--.

Claim 27, column 27, line 27, "$(C_3-C_9)$-cloalkyl," should read --$(C_3-C_9)$-cycloalkyl,--.

Claim 27, column 27, line 33, after "and", delete the comma.

UNITED STATES PATENT AND TRADEMARK OFFICE
CERTIFICATE OF CORRECTION

PATENT NO.         : 6,844,347 B1
APPLICATION NO. : 09/762893
DATED              : January 18, 2005
INVENTOR(S)        : Ursula Schindler et al.

It is certified that error appears in the above-identified patent and that said Letters Patent is hereby corrected as shown below:

Claim 27, column 27, lines 47-48, "-O-($C_1$-$C_4$) alkyl," should read
-- -O-($C_1$-$C_4$)-alkyl,--.

Claim 27, column 28, lines 1-2, "-O-($C_2$-$C_4$)-alkyl-O-($C_1$-$C_4$)alkyl," should
read -- -O-($C_2$-$C_4$)-alkyl-O-($C_1$-$C_4$)-alkyl,--.

Claim 27, column 28, line 4, "N(($C_1$-$C_4$)alkyl)$_2$," should read
--N(($C_1$-$C_4$)-alkyl)$_2$,--.

Claim 27, column 28, line 28, "aryl ($C^1$-$C^4$)-alkyl;" should read
--aryl-($C^1$-$C^4$)-alkyl;--.

Claim 27, column 28, lines 39-40, "-CO-N(($C_1$-$C_4$)-alkyl)-$_2$," should read
-- -CO-N(($C_1$-$C_4$)-alkyl)$_2$,--.

Signed and Sealed this

Tenth Day of June, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,844,347 B1 |
| APPLICATION NO. | : 09/762893 |
| DATED | : January 18, 2005 |
| INVENTOR(S) | : Ursula Schindler et al. |

It is certified that error appears in the above-identified patent and that said Letters Patent is hereby corrected as shown below:

<u>Title Page,</u>

Item (54) and Column 1, lines 1 and 2, in the Title, lines 1-2, "4-AMINO-2ARYL-PYRIMIDINES" should read --4-AMINO-2-ARYL-PYRIMIDINES--.

Item (75), line 1, "Ursula Schnidler" should read --Ursula Schindler--.

<u>Claims</u>

Claim 16, column 14, line 32, "claim 15" should read --claim 12,--.

Claim 1, column 19, line 61, "-O($C_2$-$C_4$)-alkyl-O-($C_1$-$C_4$)-alkyl," should read -- -O-($C_2$-$C_4$)-alkyl-O-($C_1$-$C_4$)-alkyl,--.

Claim 1, column 19, lines 66-67, "-CO-($C_1$-$C_4$) -alkyl;" should read -- -CO-($C_1$-$C_4$)-alkyl;--.

Claim 1, column 20, line 42, "-CO-NH-($C_1$-$C_4$)alkyl," should read -- -CO-NH-($C_1$-$C_4$)-alkyl,--.

Claim 2, column 21, lines 20-21, "($C_1$-$C_4$) alkyl-S(O)$_m$-," should read --($C_1$-$C_4$)-alkyl-S(O)$_m$-,--.

Claim 3, column 21, lines 38-39, "($C_3$-$C_9$) cycloalkyl," should read --($C_3$-$C_9$)-cycloalkyl,--.

Claim 6, column 22, line 8, "S(O))$_m$" should read --S(O)$_m$--.

Claim 6, column 22, lines 13-14, "($C_1$-$C_4$) -alkyl-S(O)$_m$-," should read --($C_1$-$C_4$)-alkyl-S(O)$_m$-,--.

Claim 6, column 22, line 35, "-O-($C_2$-$C_4$)-alkyl, -O-($C_1$-$C_4$)-alkyl," should read -- -O-($C_2$-$C_4$)-alkyl-O-($C_1$-$C_4$)-alkyl,--.

Claim 6, column 22, line 36, "$NH_2$-NH-($C_1$-$C_4$)-alkyl," should read --$NH_2$, -NH-($C_1$-$C_4$)-alkyl,--.

Claim 6, column 22, line 40, "-CO-O-($C_2$-$C_4$)-alkyl," should read -- -CO-O-($C_1$-$C_4$)-alkyl,--.

Claim 6, column 22, line 42, "($C_1$-$C_5$)-alkyl," should read --($C_2$-$C_5$)-alkyl,--.

UNITED STATES PATENT AND TRADEMARK OFFICE
CERTIFICATE OF CORRECTION

PATENT NO. : 6,844,347 B1
APPLICATION NO. : 09/762893
DATED : January 18, 2005
INVENTOR(S) : Ursula Schindler et al.

It is certified that error appears in the above-identified patent and that said Letters Patent is hereby corrected as shown below:

Claim 6, column 22, lines 46-47, after "($C_1$-$C_2$)-alkylenedioxy", insert a comma.

Claim 6, column 23, line 11, "($C_1$-$C_4$)alkyl," should read --($C_1$-$C_4$)-alkyl,--.

Claim 6, column 23, lines 14-15, "-N(($C_1$-$C_4$)-alkyl)$_2$-NH-CHO," should read -- -N(($C_1$-$C_4$)-alkyl)$_2$, -NH-CHO,--.

Claim 11, column 23, lines 60-61, "($C_3$-$C_9$)-cloalkyl," should read --($C_3$-$C_9$)-cycloalkyl,--.

Claim 18, column 24, line 66, "4 chlorophenyl," should read --4-chlorophenyl,--.

Claim 20, column 25, line 41, "($C_3$-$C_7$)-cloalkyl," should read --($C_3$-$C_7$)-cycloalkyl,--.

Claim 20, column 25, lines 47-48, "-O-($C_1$-$C_4$) alkyl," should read -- -O-($C_1$-$C_4$)-alkyl,--.

Claim 20, column 25, lines 53-54, "-CO-($C_1$-$C_4$)alkyl;" should read -- -CO-($C_1$-$C_4$)-alkyl;--.

Claim 20, column 25, line 55, "($C_2$-$C_5$)alkyl," should read --($C_2$-$C_5$)-alkyl,--.

Claim 20, column 25, lines 58-59, "-O-($C_1$-$C_4$)-alkyl-O-($C_1$-$C_4$)-alkyl," should read -- -O-($C_2$-$C_4$)-alkyl-O-($C_1$-$C_4$)-alkyl,--.

Claim 20, column 25, line 61, "N(($C_2$-$C_4$)-alkyl)$_2$," should read --N(($C_1$-$C_4$)-alkyl)$_2$,--.

Claim 20, column 25, line 62, delete the second occurrence of "-CO-$NH_2$,".

Claim 21, column 26, in the structure for formula I between lines 14-22,

" 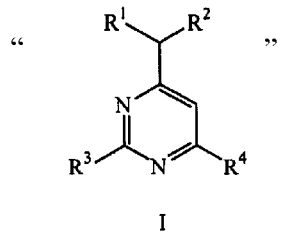 "

UNITED STATES PATENT AND TRADEMARK OFFICE
CERTIFICATE OF CORRECTION

PATENT NO. : 6,844,347 B1
APPLICATION NO. : 09/762893
DATED : January 18, 2005
INVENTOR(S) : Ursula Schindler et al.

Page 3 of 4

It is certified that error appears in the above-identified patent and that said Letters Patent is hereby corrected as shown below:

should read

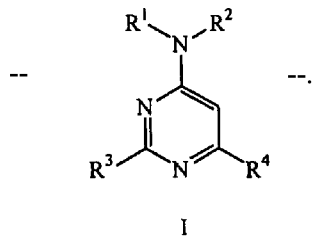

I

Claim 22, column 26, line 30, "comprises-activating" should read --comprises activating--.

Claim 22, column 26, in the structure for formula I between lines 37-45,

" 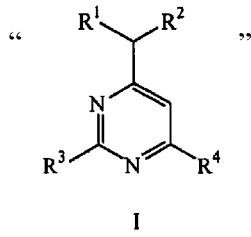 "

I should read

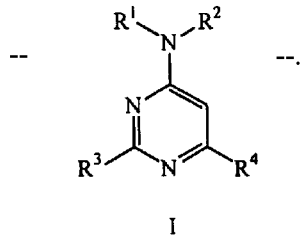

I

Claim 27, column 27, line 23, "aryl-$(C_1-C_4)$-alkyl;" should read --aryl-$(C_1-C_4)$-alkyl-;--.

Claim 27, column 27, line 27, "$(C_3-C_9)$-cloalkyl," should read --$(C_3-C_9)$-cycloalkyl,--.

Claim 27, column 27, line 33, after "and", delete the comma.

UNITED STATES PATENT AND TRADEMARK OFFICE
CERTIFICATE OF CORRECTION

PATENT NO. : 6,844,347 B1
APPLICATION NO. : 09/762893
DATED : January 18, 2005
INVENTOR(S) : Ursula Schindler et al.

It is certified that error appears in the above-identified patent and that said Letters Patent is hereby corrected as shown below:

Claim 27, column 27, lines 47-48, "-O-($C_1$-$C_4$) alkyl," should read
-- -O-($C_1$-$C_4$)-alkyl,--.

Claim 27, column 28, lines 1-2, "-O-($C_2$-$C_4$)-alkyl-O-($C_1$-$C_4$)alkyl," should read -- -O-($C_2$-$C_4$)-alkyl-O-($C_1$-$C_4$)-alkyl,--.

Claim 27, column 28, line 4, "N(($C_1$-$C_4$)alkyl)$_2$," should read
--N(($C_1$-$C_4$)-alkyl)$_2$,--.

Claim 27, column 28, line 28, "aryl ($C^1$-$C^4$)-alkyl;" should read
--aryl-($C^1$-$C^4$)-alkyl;--.

Claim 27, column 28, lines 39-40, "-CO-N(($C_1$-$C_4$)-alkyl)-$_2$," should read -- -CO-N(($C_1$-$C_4$)-alkyl)$_2$,--.

This certificate supersedes the Certificate of Correction issued June 10, 2008.

Signed and Sealed this

Fifteenth Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 6,844,347 B1
APPLICATION NO. : 09/762893
DATED : January 18, 2005
INVENTOR(S) : Ursula Schnidler et al.

It is certified that error appears in the above-identified patent and that said Letters Patent is hereby corrected as shown below:

Title Page,

Item (54), in the Title, lines 1-2, "4-AMINO-2ARYL-PYRIMIDINES" should read --4-AMINO-2-ARYL-PYRIMIDINES--.

Item (75), line 1, "Ursula Schnidler" should read --Ursula Schindler--.

Claims

Claim 1, column 19, line 61, "-O($C_2$-$C_4$)-alkyl-O-($C_1$-$C_4$)-alkyl," should read -- -O-($C_2$-$C_4$)-alkyl-O-($C_1$-$C_4$)-alkyl,--.

Claim 1, column 19, lines 66-67, "-CO-($C_1$-$C_4$) -alkyl;" should read -- -CO-($C_1$-$C_4$)-alkyl;--.

Claim 1, column 20, line 42, "-CO-NH-($C_1$-$C_4$)alkyl," should read -- -CO-NH-($C_1$-$C_4$)-alkyl,--.

Claim 2, column 21, lines 20-21, "($C_1$-$C_4$) alkyl-S(O)$_m$-," should read --($C_1$-$C_4$)-alky-S(O)$_m$-,--.

Claim 3, column 21, lines 38-39, "($C_3$-$C_9$) cycloalkyl," should read --($C_3$-$C_9$)-cycloalkyl,--.

Claim 6, column 22, line 8, "S(O))$_m$" should read --S(O)$_m$--.

Claim 6, column 22, lines 13-14, "($C_1$-$C_4$) -alkyl-S(O)$_m$-," should read --($C_1$-$C_4$)-alkyl-S(O)$_m$-,--.

Claim 6, column 22, line 35, "-O-($C_2$-$C_4$)-alkyl, -O-($C_1$-$C_4$)-alkyl," should read -- -O-($C_2$-$C_4$)-alkyl-O-($C_1$-$C_4$)-alkyl,--.

Claim 6, column 22, line 36, "$NH_2$-NH-($C_1$-$C_4$)-alkyl," should read --$NH_2$, -NH-($C_1$-$C_4$)-alkyl,--.

Claim 6, column 22, line 40, "-CO-O-($C_2$-$C_4$)-alkyl," should read -- -CO-O-($C_1$-$C_4$)-alkyl,--.

UNITED STATES PATENT AND TRADEMARK OFFICE
CERTIFICATE OF CORRECTION

PATENT NO. : 6,844,347 B1
APPLICATION NO. : 09/762893
DATED : January 18, 2005
INVENTOR(S) : Ursula Schnidler et al.

It is certified that error appears in the above-identified patent and that said Letters Patent is hereby corrected as shown below:

Claim 6, column 22, line 42, "$(C_1-C_5)$-alkyl," should read --$(C_2-C_5)$-alkyl,--.

Claim 6, column 22, lines 46-47, after "$(C_1-C_2)$-alkylenedioxy", insert a comma.

Claim 6, column 23, line 11, "$(C_1-C_4)$alkyl," should read --$(C_1-C_4)$-alkyl,--.

Claim 6, column 23, lines 14-15, "-$N((C_1-C_4)$-alkyl$)_2$-NH-CHO," should read -- -$N((C_1-C_4)$-alkyl$)_2$, -NH-CHO,--.

Claim 11, column 23, lines 60-61, "$(C_3-C_9)$-cloalkyl," should read --$(C_3-C_9)$-cycloalkyl,--.

Claim 18, column 24, line 66, "4 chlorophenyl," should read --4-chlorophenyl,--.

Claim 20, column 25, line 41, "$(C_3-C_7)$-cloalkyl," should read --$(C_3-C_7)$-cycloalkyl,--.

Claim 20, column 25, lines 47-48, "-O-$(C_1-C_4)$ alkyl," should read -- -O-$(C_1-C_4)$-alkyl,--.

Claim 20, column 25, lines 53-54, "-CO-$(C_1-C_4)$alkyl;" should read -- -CO-$(C_1-C_4)$-alkyl;--.

Claim 20, column 25, line 55, "$(C_2-C_5)$alkyl," should read --$(C_2-C_5)$-alkyl,--.

Claim 20, column 25, lines 58-59, "-O-$(C_1-C_4)$-alkyl-O-$(C_1-C_4)$-alkyl," should read -- -O-$(C_2-C_4)$-alkyl-O-$(C_1-C_4)$-alkyl,--.

Claim 20, column 25, line 61, "$N((C_2-C_4)$-alkyl$)_2$," should read --$N((C_1-C_4)$-alkyl$)_2$,--.

Claim 20, column 25, line 62, delete the second occurrence of "-CO-$NH_2$,".

UNITED STATES PATENT AND TRADEMARK OFFICE
CERTIFICATE OF CORRECTION

PATENT NO.       : 6,844,347 B1                              Page 3 of 5
APPLICATION NO. : 09/762893
DATED            : January 18, 2005
INVENTOR(S)      : Ursula Schnidler et al.

It is certified that error appears in the above-identified patent and that said Letters Patent is hereby corrected as shown below:

Claim 21, column 26, in the structure for formula I between lines 14-22,

"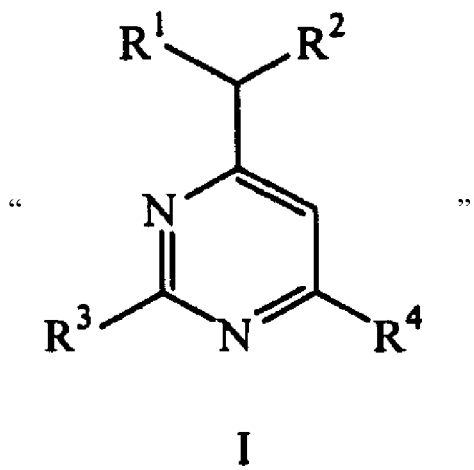"

should read

--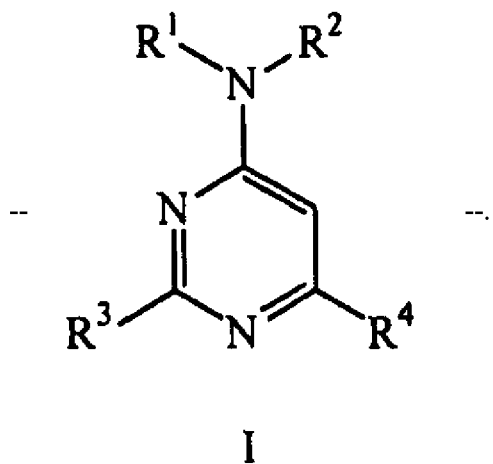--.

Claim 22, column 26, line 30, "comprises-activating" should read
--comprises activating--.

UNITED STATES PATENT AND TRADEMARK OFFICE
CERTIFICATE OF CORRECTION

PATENT NO.         : 6,844,347 B1
APPLICATION NO.    : 09/762893
DATED              : January 18, 2005
INVENTOR(S)        : Ursula Schnidler et al.

It is certified that error appears in the above-identified patent and that said Letters Patent is hereby corrected as shown below:

Claim 22, column 26, in the structure for formula I between lines 37-45,

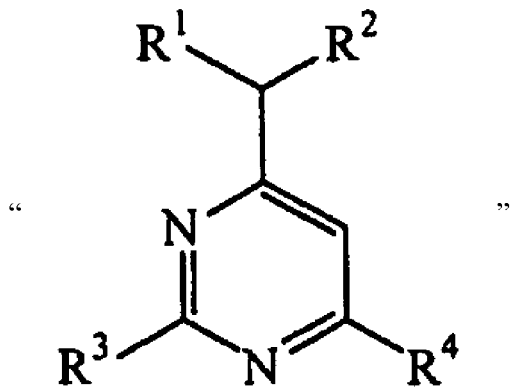

"

"

I should read

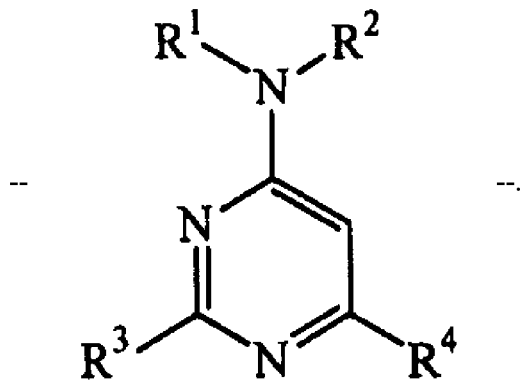

--

--.

I

Claim 27, column 27, lines 23, "aryl-($C_1$-$C_4$)-alkyl;" should read
--aryl-($C_1$-$C_4$)-alkyl-;--.

UNITED STATES PATENT AND TRADEMARK OFFICE
CERTIFICATE OF CORRECTION

| | |
|---|---|
| PATENT NO. | : 6,844,347 B1 |
| APPLICATION NO. | : 09/762893 |
| DATED | : January 18, 2005 |
| INVENTOR(S) | : Ursula Schnidler et al. |

It is certified that error appears in the above-identified patent and that said Letters Patent is hereby corrected as shown below:

Claim 27, column 27, line 27, "$(C_3-C_9)$-cloalkyl," should read --$(C_3-C_9)$-cycloalkyl,--.

Claim 27, column 27, line 33, after "and", delete the comma.

Claim 27, column 27, lines 47-48, "-O-$(C_1-C_4)$ alkyl," should read -- -O-$(C_1-C_4)$-alkyl,--.

Claim 27, column 28, lines 1-2, "-O-$(C_2-C_4)$-alkyl-O-$(C_1-C_4)$alkyl," should read -- -O-$(C_2-C_4)$-alkyl-O-$(C_1-C_4)$-alkyl,--.

Claim 27, column 28, line 4, "N($(C_1-C_4)$alkyl)$_2$," should read --N($(C_1-C_4)$-alkyl)$_2$,--.

Claim 27, column 28, line 28, "aryl $(C^1-C^4)$-alkyl;" should read --aryl-$(C^1-C^4)$-alkyl;--.

Claim 27, column 28, lines 39-40, "-CO-N($(C_1-C_4)$-alkyl)-$_2$," should read -- -CO-N($(C_1-C_4)$-alkyl)$_2$,--.

Signed and Sealed this

Twelfth Day of August, 2008

JON W. DUDAS
*Director of the United States Patent and Trademark Office*